(12) United States Patent
Pierstorff et al.

(10) Patent No.: US 9,040,071 B2
(45) Date of Patent: May 26, 2015

(54) PARY-XYLENE BASED MICROFILM ELUTION DEVICES

(71) Applicant: Cute Lovable Teddy Bear, LLC., Los Angeles, CA (US)

(72) Inventors: Erik Pierstorff, Playa Del Ray, CA (US); Christian Behrenbruch, Los Angeles, CA (US); Edward Chow, San Francisco, CA (US); Dean Ho, Chicago, IL (US)

(73) Assignee: Cute Lovable Teddy Bear, LLC., Los Angeles, CA (US)

( * ) Notice: Subject to any disclaimer, the term of this patent is extended or adjusted under 35 U.S.C. 154(b) by 0 days.

(21) Appl. No.: 14/260,299

(22) Filed: Apr. 24, 2014

(65) Prior Publication Data

US 2014/0236080 A1 Aug. 21, 2014

Related U.S. Application Data

(63) Continuation of application No. 13/380,520, filed as application No. PCT/US2009/048974 on Jun. 27, 2009, now Pat. No. 8,709,467.

(51) Int. Cl.
*A61K 47/32* (2006.01)
*A61K 9/00* (2006.01)
(Continued)

(52) U.S. Cl.
CPC ............... *A61K 47/32* (2013.01); *A61K 9/0024* (2013.01); *A61K 9/2086* (2013.01); *A61K 9/7007* (2013.01); *A61L 15/24* (2013.01);
(Continued)

(58) Field of Classification Search
CPC .............................. A61K 57/32; A61K 9/7007
See application file for complete search history.

(56) References Cited

U.S. PATENT DOCUMENTS

| 5,609,629 A | 3/1997 | Fearnot et al. |
| 6,419,692 B1 | 7/2002 | Yang et al. |

(Continued)

FOREIGN PATENT DOCUMENTS

| WO | 2008/039749 A2 | 7/2008 |
| WO | 2008/091925 A2 | 7/2008 |

OTHER PUBLICATIONS

L. Wolgemuth, (Coatings) A Look at Parylene Coatings in Drug-Eluting Technology, Medical Device & Diagnostic Industries, 2005, www.devicelink.com/mddi/archive/05/08/004.html.
(Continued)

*Primary Examiner* — Benjamin Packard
(74) *Attorney, Agent, or Firm* — Howard L. Hoffenberg; IP and Business Law Offices of Howard L. Hoffenberg, Esq

(57) ABSTRACT

This invention is in the field of controlled elution devices for therapeutic delivery. There exists a need for a stand-alone capable device for the localized and extended delivery of a therapeutic. This need is overcome by the present invention having an examplary embodiment comprised of a microfilm base (12), a reservoir of a therapeutic (14) disposed about the microfilm base (12) and a top layer (24) that is (i) a plurality of laminated layers (24) of para-xylyelne polymer and/or (ii) para-xylyelne polymer endowed with oxidatively functionalized para-xyele units. The thicknesses of the device is optimally in the range of about 10 to about 200 microns. The device is usable for the localized release of broad spectrum therapeutics for interventional and preventative medicine.

7 Claims, 19 Drawing Sheets

(51) Int. Cl.
    *A61K 9/20*     (2006.01)
    *A61K 9/70*     (2006.01)
    *A61L 15/24*    (2006.01)
    *A61L 15/42*    (2006.01)
    *A61L 15/44*    (2006.01)

(52) U.S. Cl.
    CPC .............. *A61L 15/425* (2013.01); *A61L 15/44* (2013.01); *A61L 2300/416* (2013.01); *A61L 2300/426* (2013.01); *A61L 2300/43* (2013.01); *A61L 2300/602* (2013.01); *A61L 2300/608* (2013.01)

(56) References Cited

U.S. PATENT DOCUMENTS

| | | |
|---|---|---|
| 6,656,156 B2 | 12/2003 | Yang et al. |
| 6,695,833 B1 | 2/2004 | Frantzen |
| 7,077,859 B2 | 7/2006 | Sirh et al. |
| 7,163,715 B1 | 1/2007 | Kramer |
| 7,175,611 B2 | 2/2007 | Mitchnick |
| 7,303,758 B2 | 12/2007 | Palotico et al. |
| 7,445,628 B2 | 11/2008 | Ragheb et al. |
| 2005/0033414 A1 | 2/2005 | Zhang et al. |
| 2005/0038472 A1 | 2/2005 | Furst |
| 2005/0043788 A1 | 2/2005 | Luo et al. |
| 2005/0177225 A1 | 8/2005 | Hunter et al. |
| 2008/1810090 | 8/2005 | Hunter |
| 2005/0281858 A1 | 12/2005 | Kloke |
| 2006/0083770 A1 | 4/2006 | Greiner et al. |
| 2006/0265049 A1 | 11/2006 | Gray et al. |
| 2007/0150047 A1 | 6/2007 | Ruane et al. |
| 2007/0299043 A1 | 12/2007 | Hunter et al. |
| 2008/0075753 A1 | 3/2008 | Chappa |
| 2008/0181930 A1 | 7/2008 | Rodstrom et al. |
| 2008/0215138 A1 | 9/2008 | Bates et al. |
| 2008/0302675 A1 | 12/2008 | Hsiai et al. |
| 2009/0004241 A1 | 1/2009 | Ho et al. |

OTHER PUBLICATIONS

E. Perstorff et al, Nanoscale architectural tuning of parylene patch devices to control therapeutic release rates, Nanotechnology, 2008, 19, 445104 (8pp), IOP 1 Publishing Ltd., UK, stacks.iop.org/Nano/19/445104.

G.Miralles, International Search Report, Mar. 31, 2010, PCT/US2009/048974, World Intellectual Property Organization.

OR

PARY-XYLENE BASED MICROFILM ELUTION DEVICES

CROSS-REFERENCES TO RELATED APPLICATIONS

This application is a continuation of and claims the benefit of copending U.S. application Ser. No. 13/380,520, filed on Dec. 22, 2011, for which the entirety and full disclosure is incorporated by reference, which is a 371 continuation of now abandoned International Application PCT/US/0948974 filed on Jun. 27, 2009, for which the entirety and full disclosure is incorporated by reference.

TECHNICAL FIELD

This invention pertains generally to controlled elution devices for therapeutic delivery and more particularly to controlled elution devices using a porous parylene barrier layer.

BACKGROUND ART

In treating certain unhealthy conditions, including several categories of severe illness, it is highly desirable to localize or target delivery of a therapeutic to a tissue or organ in need of treatment. This is so for three main reasons. One reason is that the therapeutic has toxic and/or adverse side effect(s) and systemic delivery is deleterious; e.g., this is particularly the case with chemotherapy. The second reason is that the therapeutic is very expensive; e.g., this is particularly the case with biologics. The third reason is that effective treatment requires a high dosage.

It is known in the art to localize or target the delivering of a therapeutic by linking the therapeutic to an antibody and/or ligand for a cell surface receptor. This technology has the disadvantages of a lack of specificity of the monoclonal antibody or ligand to exclusively target a tissue or organ, a micro environment surrounding the tissue or organ that restricts or inhibits access by the antibody or ligand linked therapeutic and an adverse immune response to the antibody or ligand linked therapeutic.

Changing the subject to a different aspect of the delivery of a therapeutic, there is often in pharmacokinetics a time-dose relationship in order to achieve a desired therapeutic effect. Hence, controlled elution devices have been developed that provide for the time extended delivery of some therapeutics. Notwithstanding, there exist a wide range of therapeutics for which time extended delivery by current means is not possible or for which a limited time-dose delivery can be achieved which in turn limits effectiveness or results in side effects.

It is known in the art to construct controlled elution devices using parylene C and other derivatives of parylene. Parylene C is a USP class VI biocompatible material and is certified nontoxic. The atomic composition of Parylene C is a carbon, hydrogen and chlorine. The chemical structure is a chain of chlorinated xylenes. That is, methylated benzene ring with a chlorine atom on the benzene ring that are connected by their methyl groups such that the methyl groups serve as connecting bridges.

A review of what was known in the art as of 2005 is presented in L. Wolgemuth., "A Look at Parylene Coatings in Drug-Eluting Technologies," Medical Device & Diagnostic Industry Magazine, (August, 2005.) Wolgemuth wrote that "Manufacturers can also manipulate the thickness of the coating [of parylene] to very thin, porous layers and vary the ratio of drug to parylene in a multiple-layer construct. These attributes enable it to provide control of the drug-delivery rate. The parylene coating can be applied over the drug-coated stent surfaces (drug application is not a part of the vapor-deposition polymerization process) in layers sufficiently thin such that its matrix structure becomes open and porous. At these angstrom thickness levels, parylene allows drug molecules to pass through it at a rate that is a function of film thickness and drug molecule size. [paragraph] In a multilayer device, for example, a drug-to-carrier polymer ratio that is higher in the interior layers than in the external layers could result in a lower initial dose delivery and in a total dose that would be delivered more uniformly and over a sustained period." This technology has the disadvantages of not being directed at a standalone capable device, not overcoming failures that occur in a coating that is flexible and undergoes deformation, not being tunable to achieve particular elution profiles, lacking accuracy and not accommodating a wide spectrum of therapeutics.

Known in the art is a parylene based controlled elution device in connection with a medical device (namely, a stent) as taught by U.S. Pat. No. 7,445,628 B2 by Ragheb et al. assigned to Cook Incorporated and US Patent Application Publication US2007/0150047 A1 by Ruane et al. assigned to Cook Incorporated (hereafter collectively "Cook.") These patents disclose a first coating layer of parylene posited on the stent. On at least a portion of this coated structure, there is a layer comprising a bioactive; namely, an immunosurpressive agent or paclitaxel. Overlying this layer, there is a porous layer of a parylene derivative in a thickness between 5,000 to 250,000 Angstroms (i.e., $5 \times 10^{-7}$ meters to $2.5 \times 10^{-5}$ meters; 0.5 to 25 microns or 500 to 25,000 nanometers.) The teaching of Cook has the disadvantage of not being directed at a standalone capable device, not overcoming failures that occur in a coating that is flexible and undergoes deformation, not being tunable to achieve particular elution profiles, lacking accuracy and not accommodating a wide spectrum of therapeutics.

Known in the art is a parylene based controlled elution device in connection with a medical device (namely, a stent) as taught by US Patent Application Publication US2005/0033414 A1 by Zhang et al. and assigned to Microport Medical Co., Ltd. and US Patent Application Publication US2005/0043788 A1 by Luo et al. and assigned to Microport Medical Co., Ltd. (hereafter collectively "Microport.") These patents disclose a stent is coated with a primer. There are one or more overlying drug layers. On top of the drug layer(s) is coated a controlled releasing barrier layer. The thickness of the entire coating is between 0.1 to 100 microns. There is a discloser of data for the release rates of different molecular weight drugs (Cilostazol and Rapamycin) where the controlled releasing barrier layer is parylene. There is a disclosure of data for the release rates of camptothecin where the controlled releasing barrier layer is a parylene coating having a thickness that is 0.05 microns, 0.1 microns, 0.2 microns, 0.4 microns or 0.5 microns. The teaching of Microport has the disadvantage of not being directed at a standalone capable device, not overcoming failures that occur in a coating that is flexible and undergoes deformation, not being tunable to achieve particular elution profiles, lacking accuracy and not accommodating a wide spectrum of therapeutics.

A deficiency in the art is a standalone controlled elution device (not supported by a medical device) that is flexible, resistant to tearing and resistant to delamination. Another deficiency in the art is a mechanism for the time extended delivery that is suitable for a broad spectrum of therapeutics or combination of therapeutics. Another deficiency in the art is a mechanism for accurately controlling the time extended delivery of certain therapeutics or combination of therapeutics. Another deficiency in the art is a tunable parylene controlled elution device to achieve certain needed elution profiles.

There exists a need for standalone controlled elution device in a usable size that is flexible and can undergo deformation without significant delamination and/or tearing. There is a sub-need for a controlled elution that is standalone capable that can be disposed in vivo on an organ or tissue for the localized and/or targeted delivery of a therapeutic.

There exists a need for a controlled elution device for certain therapeutics or combination of therapeutics for which current devices are not capable of delivering extended release in a clinically meaningful way. There is a particularized sub-need for controlled elution devices to deliver hormone replacement or adjunct therapy.

There exists a need for a controlled elution device that is tunable to achieve a particular elution profiles that have heretofore been unachievable in a clinically meaningful way.

There exists a need for a controlled elution device that more accurately and/or with greater control delivers a therapeutic or combination of therapeutics.

There exists a need for a controlled elution device that is simplified with no overlying barrier layer.

There exists a need for solutions to the above deficiencies in the art that are cost effective in the market for healthcare.

The present invention satisfies these needs, as well as others, and generally overcomes the presently known deficiencies in the art.

SUMMARY OF THE INVENTION

The present invention is directed to parylene based controlled elution devices for the time extended delivery of a therapeutic or combination of therapeutics.

An object of the present invention is a standalone controlled elution device in a usable size that is flexible and can undergo deformation without significant delamination and/or tearing.

Another object of the present invention is a controlled elution that is standalone capable that can be disposed in vivo on an organ or tissue. A sub-objective is a controlled elution device for the localized and/or target delivery of a therapeutic.

Another object of the present invention is a controlled elution device for certain therapeutics or combination of therapeutics for which current devices are not capable of delivering extended release in a clinically meaningful way. There is a particularized sub-objective of a controlled elution device to deliver hormone replacement or adjunct therapy.

Another object of the present invention is a controlled elution device that is tunable to achieve a particular elution profiles that have heretofore been unachievable in a clinically meaningful way.

Another object of the present invention is a controlled elution device that more accurately and/or with greater control delivers a therapeutic or combination of therapeutics.

Another object of the present invention is a controlled elution device that is simplified with no overlying barrier layer.

Another object of the present invention is controlled elution devices that are cost effective in the market for healthcare.

One aspect of the present invention is a stand-alone controlled elution device. This device has a reservoir of at least one therapeutic. This reservoir is encapsulated by a microfilm that is porous that is fabricated out of para-xylylene polymer endowed with oxidatively functionalized para-xylene units.

Typically, oxidatively functionalized para-xylene units are para-xylene derivatized with one or more functional groups selected from the group consisting of —OH, —C=O, —CO—, —COOH, or —COO—, the latter carboxyl groups formed either by oxidatively functionalizing the para-xylene methyl group or by breaking the benzene through oxidative functionalization.

The therapeutic is selectable from a wide range of therapeutic classes that includes, but is not limited to, cancer treatments, inflammatory suppression, anti-viral applications, wound healing, scar formation suppression, nutrients, pain management agents and the like.

The technology is intended for sub-cutaneous implantation, on-organ deposition, and other potential routes of delivery depending upon the application.

Another aspect present invention is a stand-alone controlled elution device. The device has a reservoir of at least one therapeutic. This reservoir is encapsulated by a microfilm that is porous that is a plurality of laminated layers of para-xylylene polymer.

Another aspect of the present invention is a stand-alone capable controlled elution device. The device has a microfilm base made out of para-xylylene polymer endowed with oxidatively functionalized para-xylene units. At least one therapeutic is disposed about the microfilm base.

Another aspect of the present invention is a stand-alone capable controlled elution device. This device has a microfilm base fabricated from para-xylylene polymer having a surface endowed with para-xylene units derivatized with one or more functional groups selected from the group consisting of —OH, —COOH, —COO—, —C=O, or —CO—. At least one therapeutic is disposed about the microfilm base. The device has a thickness between about 10 microns to about 200 microns.

Another aspect of the present invention is a controlled elution device capable of mounting on a medical device. The device has a base. Disposed about this base is a reservoir of at least one therapeutic. Disposed about the reservoir is a multilayer laminate that is porous comprised of a plurality of para-xylylene polymer laminated layers.

Another aspect of the present invention is a stand-alone capable controlled elution device. The device has a microfilm base. Disposed about this base is a reservoir of at least one therapeutic. Disposed about this reservoir is a multilayer laminate that is porous. The multilayer laminate has a plurality of layers of para-xylylene polymer where at least one of the layers is comprised of para-xylylene polymer endowed with oxidatively functionalized para-xylene units.

Another aspect of the present invention is a stand-alone capable controlled elution device. This device has a microfilm base. Disposed about this base is a reservoir of at least one therapeutic. Disposed about the reservoir is a multilayer laminate that is porous disposed. The multilayer laminate has a plurality of layers of para-xylylene polymer. Each of the laminate layers is between about 5 to about 5000 nanometers thick. At least one the laminate layers is comprised of para-xylylene polymer having a surface endowed with para-xylene units derivatized with one or more functional groups selected from the group consisting of —OH, —COOH, —COO—, —C=O, or —CO—. The device has an overall thickness between about 10 microns to about 200 microns.

Another aspect of the present invention is a stand-alone capable controlled elution device. This device has a first bilayer. This first bilayer is comprised of a microfilm base and a reservoir of at least one therapeutic disposed about the microfilm base. There are one or more additional bilayers in an overlying arrangement. Each of these additional bilayers is comprised of a reservoir of at least one therapeutic and a microfilm that is porous that is disposed about the reservoir. At least one of the aforementioned microfilms is selected from the group consisting of a microfilm that is multilayer laminate of a plurality of layers of para-xylylene polymer and a microfilm comprised of para-xylylene polymer endowed with oxidatively functionalized para-xylene units.

Another aspect of the present invention is a stand-alone capable controlled elution device. This device has a central base microfilm having a first side and a second side. There is a first reservoir of at least one therapeutic disposed about the first side of the microfilm base. Disposed about this first reservoir is first multilayer laminate that is porous and has a plurality of layers of para-xylylene polymer. There is a second reservoir of at least one therapeutic disposed about the second side of the microfilm base. Disposed about the second reservoir is a second multilayer laminate that is porous and has a plurality of layers of para-xylylene polymer.

Another aspect of the present invention is a method of administering a therapeutic treatment. One step of the method is obtaining a controlled elution device as previously described. Another step is the implanting of the controlled elution device into a life form. The life form is preferably plant, veterinary animal and/or human.

Another aspect of the present is a method of administering a therapeutic treatment. One of the steps of the method is obtaining a controlled elution device as previously described. Another step is selecting an area of dermis of a life form to topically receive the device so as to be administered the therapeutic. Another step is applying a solvating liquid about the area of dermis. Another step is topically receiving the device about the area of dermis.

Another aspect of the present is the controlled elution component of a dental patch that is a controlled elution device as previously described.

Another aspect of the present is the controlled elution component of an ocular implant that is a controlled elution device as previously described.

Another aspect of the present is the controlled elution component of a medicated stent that is a controlled elution device as previously described.

Another aspect of the present is the controlled elution component of an active implanted device that is a controlled elution device as previously described.

Another aspect of the present is the controlled elution component of a breast implant that is a controlled elution device as previously described.

The previously described versions of the present invention has many advantages which include a stand alone controlled elution device that is flexible, resists tearing and resists delamination that can be disposed on a particular tissue or an organ for localized and/or targeted delivery of a therapeutic or combination of therapeutics to that tissue or organ in a controllable and accurate fashion. A more narrow advantage is disposing said device on a diseased organ or tissue; for example, hormone replacement therapy.

The previously described versions of the present invention has many advantages which include a controlled elution that can be integrated with a wide spectrum of therapeutics that can potentially alleviate or cure serious diseases and infections for which delivery by current means is either not possible, results in serious side effects and/or is of limited efficacy. There is a particularized sub-advantage of a controlled elution device to deliver hormone replacement or adjunct therapy.

The previously described versions of the present invention have advantages which include providing clinicians with a controlled elution device that can limit the number of treatments a patient requires for complex, highly toxic therapeutics, as well as improve quality of life for patients following such treatments.

The previously described versions of the present invention have many advantages which include cost effectiveness; that is, versions of the present invention provide a low-cost, customizable microfilm therapeutic delivery systems and concomitantly, reduce side effects related to therapeutic delivery and/or increase the effective therapeutic delivery time period.

BRIEF DESCRIPTION OF THE DRAWINGS

These and other features, aspects and advantages of the present invention will become better understood with reference to the following description, appended claims and accompanying drawings where:

DESCRIPTION OF EMBODIMENTS

Figure 1A:
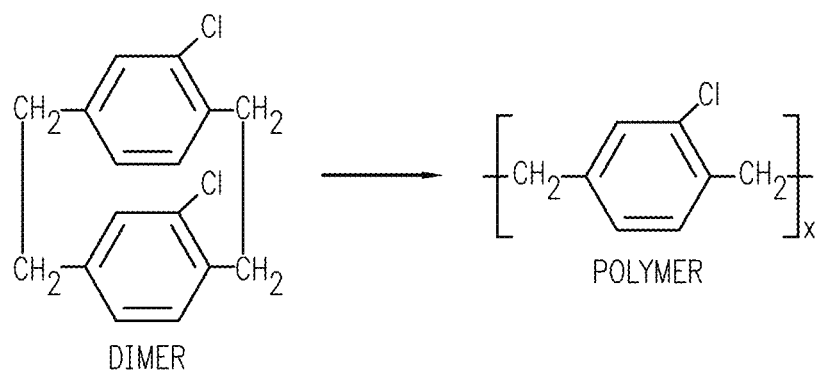
FIGS. 1A, B, C, D, E and F are stick drawings of Parylene C, Parylene A, Parylene A M, Parylene D, Parylene N and HT-Parylene (also known as Parylene F), respectively.
Figure 1B:
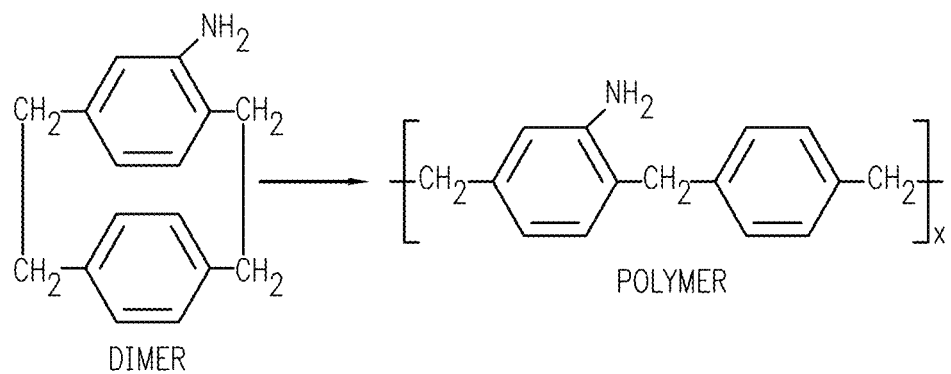
Figure 1C:
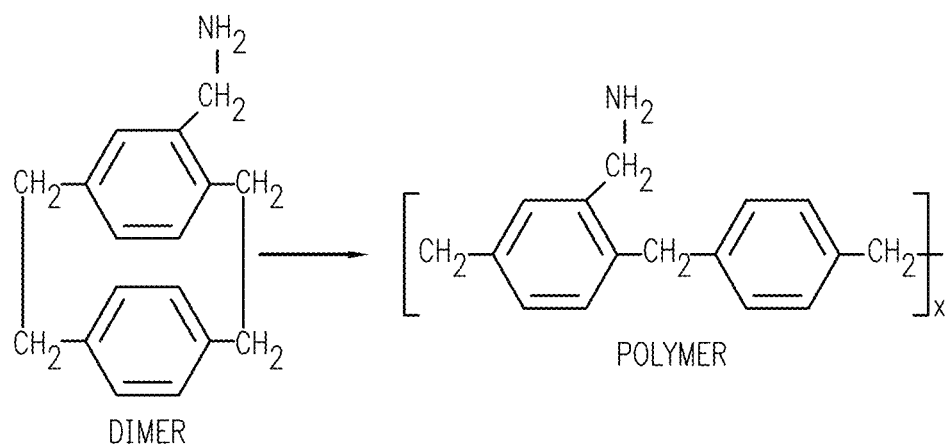
Figure 1D:
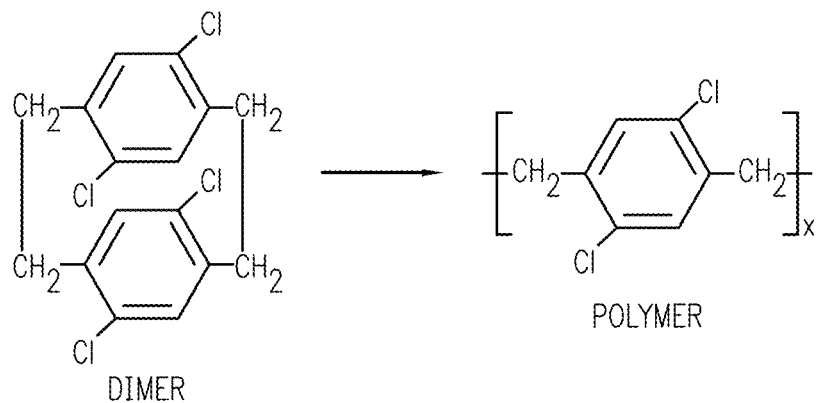
Figure 1E:
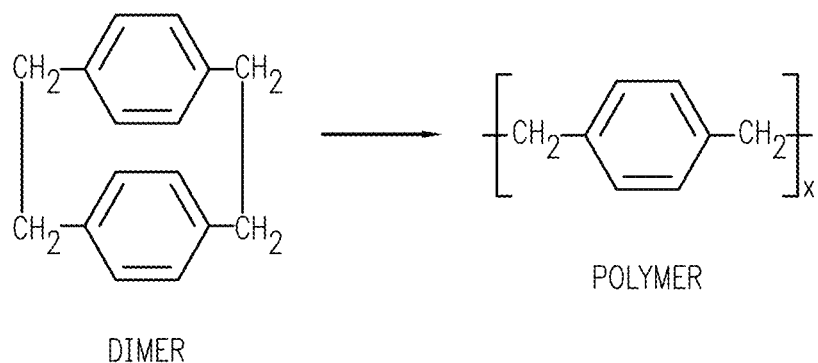
Figure 1F:
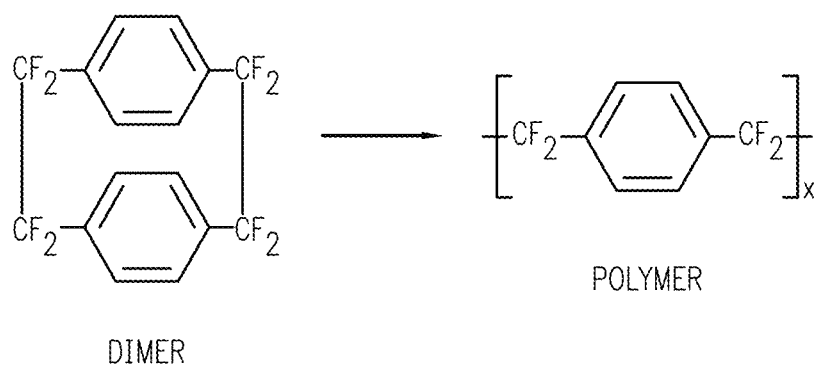

The present invention is described more fully in the following disclosure. In this disclosure, there is a discussion of embodiments of the invention and references to the accompanying drawings in which embodiments of the invention are shown. These specific embodiments are provided so that this invention will be understood by those skilled in the art. This invention is not limited to the specific embodiments set forth herein below and in the drawings. The invention is embodied in many different forms and should be construed as such with reference to the appended claims.

For the purpose of a coherent discourse, there is a summary discussion of the architecture of one embodiment of a controlled elution device according to the present invention. With that discussion serving as a frame of reference, there is next a detailed discussion of elements of present invention. Then there is a more extensive discussion of the architecture of devices according to the present invention. This discussion is then followed by a discourse on how to make and use the present invention and on other matters.

As indicated, at this juncture, the architect of one embodiment is introduced to establish a frame of reference. An embodiment of this invention is a stand-alone capable controlled elution device comprised of three layers. There is a first microfilm comprised of a multilayer laminate of a plurality of distinct layers of para-xylylene polymer with oxidatively functionalized para-xylene units. An intermediate layer reservoir comprised of a therapeutic disposed about this first layer. An overlying second, top or barrier layer comprised of a porous multilayer laminate of distinct layers of para-xylylene polymer with oxidatively functionalized para-xylene units.

At this point, the discourse turns to a discussion of elements of the present invention.

Parylene's assigned name under the nomenclature of the International Union of Pure and Applied Chemistry (IUPAC) is para-xylylene polymer. The atomic composition of para-xylylene polymer is carbon and hydrogen. The chemical structure is a chain of xylene units. A "xylene" is a methylated benzene ring. In the polymer, the xylenes are connected by their methyl groups such that the methyl groups serve as connecting bridges.

Referring to FIGS. 1A, 1B, 1C, 1D, 1E and 1F parylene is typically derivatized with either a chlorine, an amine group, a methyl amine group, multiple chlorines, or consists of an unmodified xylene unit, or a xylene unit with fluorinated methyl groups and these derivatives are referred to as parylene C, parylene A, parylene AM, parylene D, parylene N and parylene HT (also known as parylene F), respectively.

Any of the derivatives of parylene are suitable for use in embodiments of the present invention. Generally, parylene C, parylene A, parylene AM, parylene D are parylene N preferred where the device is for in vivo implantation. Parylene A and parylene AM have an active amino group and are preferred where there is to covalently or ionically attach a side chain or therapeutic to the parylene.

Figure 2A:
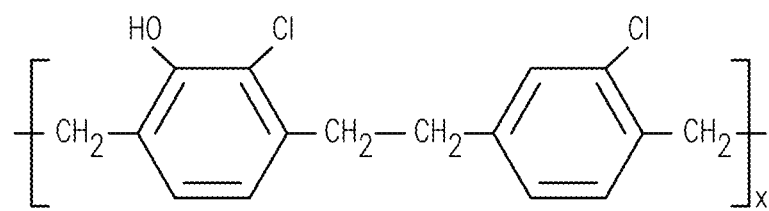
FIGS. 2A, B, and C are stick drawings of examples of oxidatively functionalized Parylene C with hydroxyl (—OH—), carbonyl (C=O), and carboxyl (—COO—), respectively.
Figure 2A:
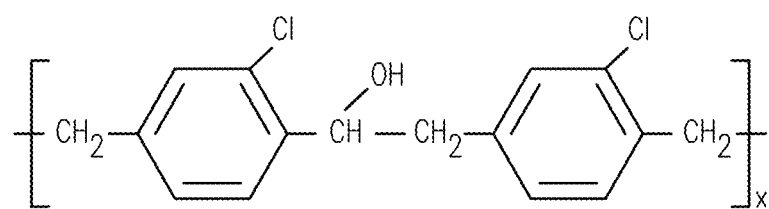
Figure 2B:
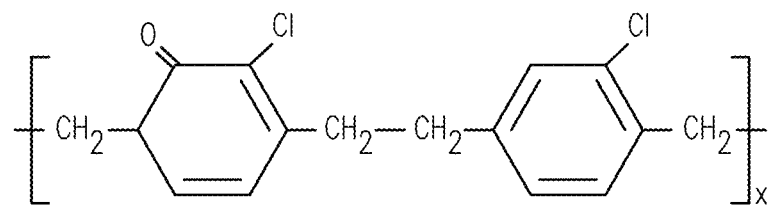
Figure 2B:
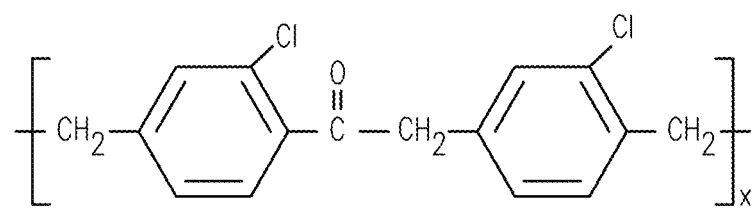
Figure 2C:
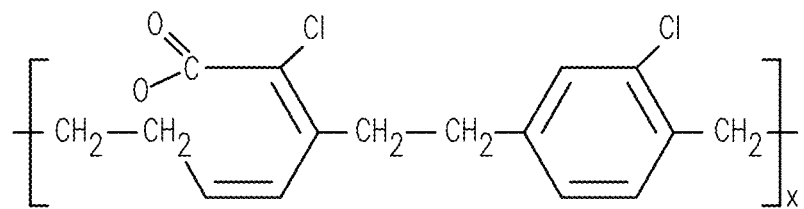
Figure 2C:
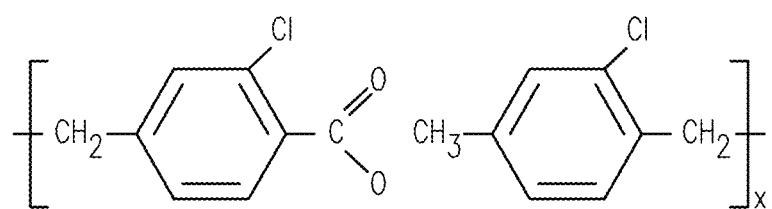

Referring to FIGS. 2A, 2B and 2C, the para-xylylene polymer used in embodiments of the present invention can be advantageously endowed with oxidatively functionalized para-xylene units. Typically, oxidatively functionalized para-xylene units are para-xylene derivatized with one or more functional groups selected from the group consisting of —OH, —C═O, —CO—, —COOH, or —COO—, the latter carboxyl groups formed either by oxidatively functionalizing the para-xylene methyl group or by breaking the benzene through oxidative functionalization. Where the para-xylylene polymer is oxidatively functionalized by oxidizing the para-xylene methyl group to a carboxyl group, the polymer chain is broken and the polymer extends in each direction from this break.

As discussed in more detail below, the endowment of para-xylylene polymer with oxidatively functionalized para-xylene units can be arc-driven, ultra violet light driven, plasma driven, chemical oxidizer driven or by any other driver for the oxidative processing of the para]xylylene.

Typically, this endowment of para-xylylene polymer with oxidatively functionalized para-xylene units yields a surface comprised of an atomic layer of oxidatively functionalized para-xylene units. The polymer mesh that is below the surface of a microfilm is generally not assessable to oxidation. There may be nooks, crannies and crevices within the mesh the expose certain below surface para-xylene units to oxidation. Generally, to have a microfilm that has a depth of oxidize para-xylene units requires utilization of the innovative technology of multi-layering as discussed below.

Referring to FIG. 3, it is believed that the endowment of para-xylylene polymer with oxidatively functionalized para-xylene units enhances wettability. Wettability pertains to the surface energy of a substrate and the surface energy of a liquid to be applied to the substrate. The difference in these surface energies determines the spread of an applied liquid to the substrate. In general, wetting increases when the surface tension of the applied liquid is much lower than that of the substrate. As used herein, wetting can also encompass the permeation of a liquid that is a solvent-solute solution or suspension into a substrate with its concomitant diffusion.

Continuing to refer to FIG. 3, wettability is experimentally measured by spotting water or other suitable liquid on a surface or substrate. A light beam is shined at a contact angle at the spotted liquid and a diffraction angle of the beam is measured. The diffraction angle is an indicator of the degree of spread of the water or liquid on the substrate surface. That is, the diffraction angle is a measure of how the water or other liquid interacts with the surface of the substrate.

Figure 3A:
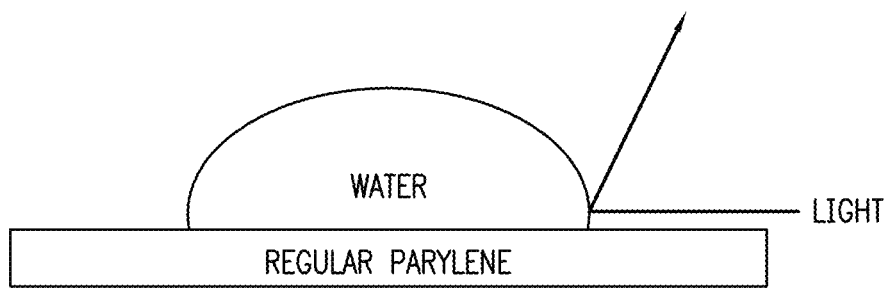
FIG. 3A is a schematic illustrating measuring wettability of a regular parylene monolayer microfilm and FIG. 3B is a schematic illustrating measuring wettability of oxidized parylene monolayer microfilm according to the present invention.
Figure 3B:
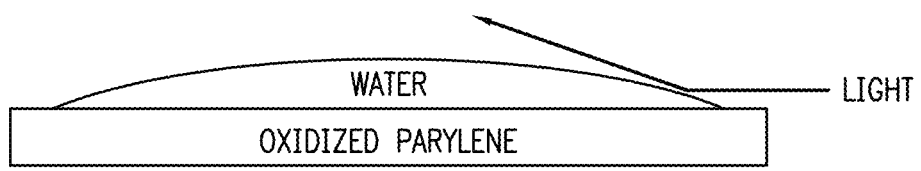

Referring to FIG. 3A, there is schematic illustration of the wetting of a liquid therapeutic or solvated dry therapeutic on a microfilm of para-xylylene polymer not endowed with oxidatively functionalized para-xylene units. With reference to FIG. 3B, the liquid therapeutic or solvated dry therapeutic undergoes relatively limited spread.

Referring to FIG. 3B, there is a schematic illustration of the wetting of a liquid therapeutic or solvated dry therapeutic on a microfilm of para-xylylene polymer endowed with oxidatively functionalized para-xylene units. With reference to FIG. 3A, the liquid therapeutic or solvated dry therapeutic undergoes a relatively greater spread.

Figure 4:
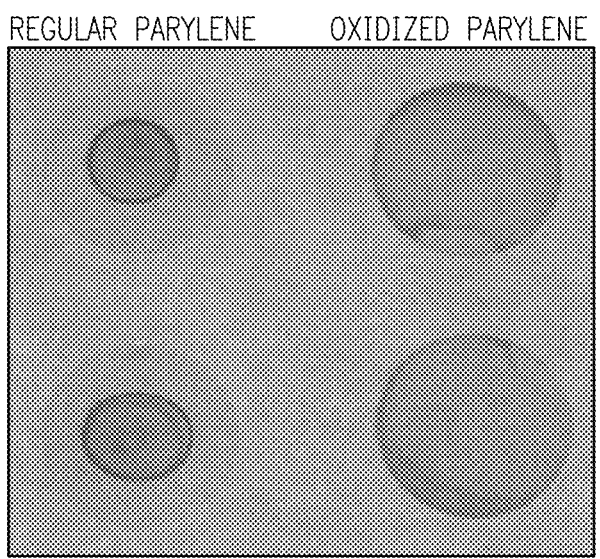
FIG. 4 are pictures showing the variation in drug spreading in unoxidized parylene monolayer microfilm (left side) and oxidatively functionalized parylene monolayer microfilm according to the present invention (right side)
Figure 5:
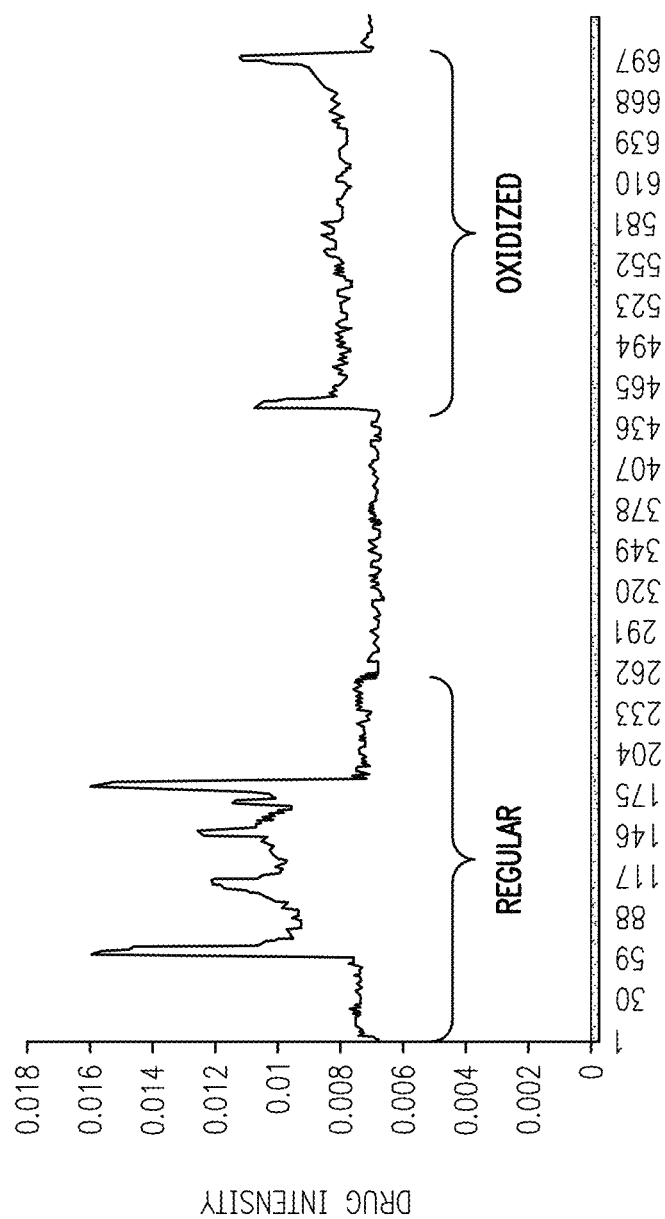
FIG. 5 is a graph showing the intensity of drug deposition in unoxidized parylene monolayer microfilm (left side) and oxidatively functionalized parylene monolayer microfilm according to present invention (right side)
Figure 6A:
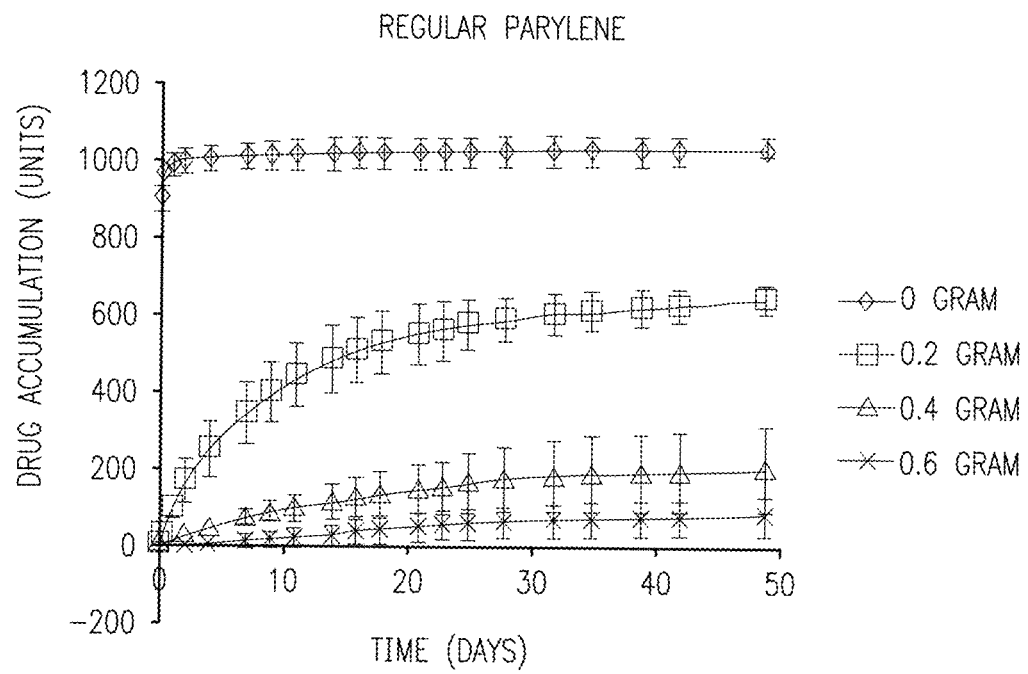
FIG. 6A is a graph showing the accumulated dexamethasone elution profiles of devices having three different thickness regular parylene barrier layer microfilms.
Figure 6B:
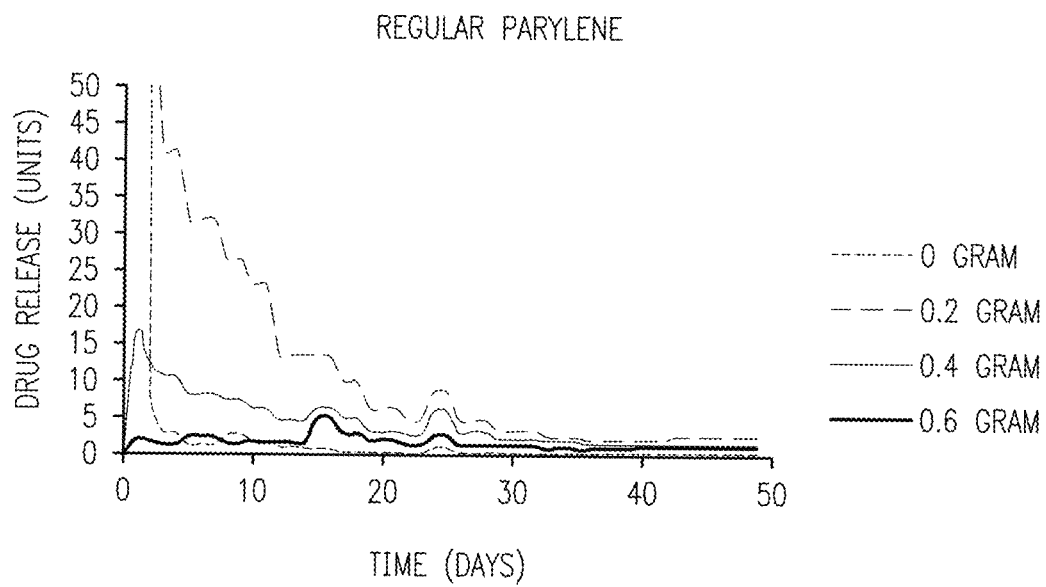
FIG. 6B is a graph showing the average dexamethasone release per day from the devices graphed in FIG. 6A.
Figure 6C:
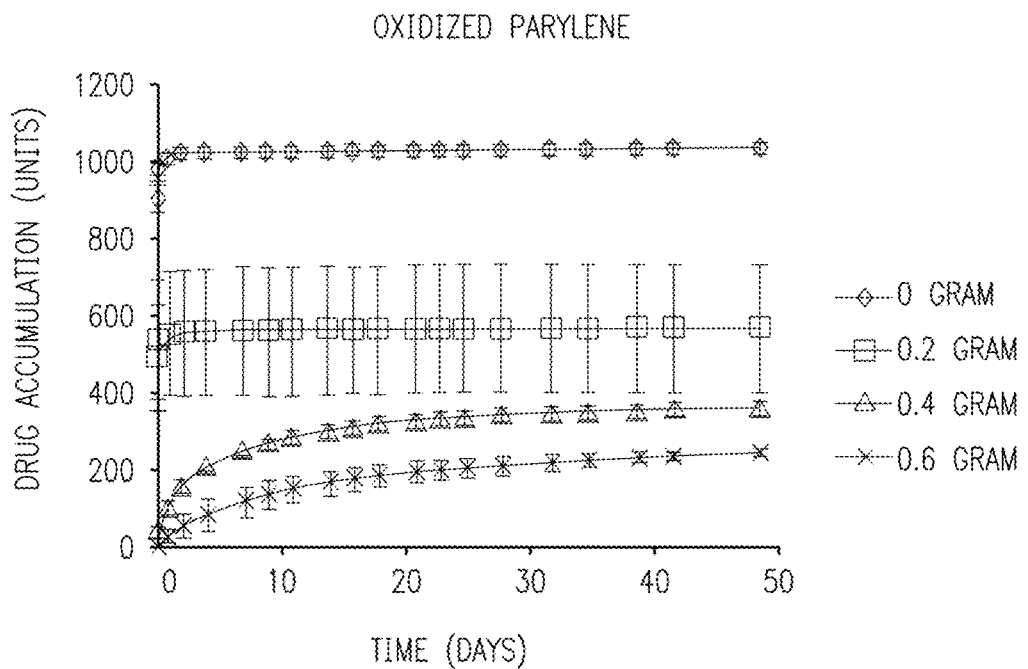
FIG. 6C is a graph showing accumulated dexamethasone elution profiles of devices having an oxidized parylene barrier layer microfilm according to the present invention and having the same thicknesses as the devices graphed in FIG. 6A.
Figure 6D:
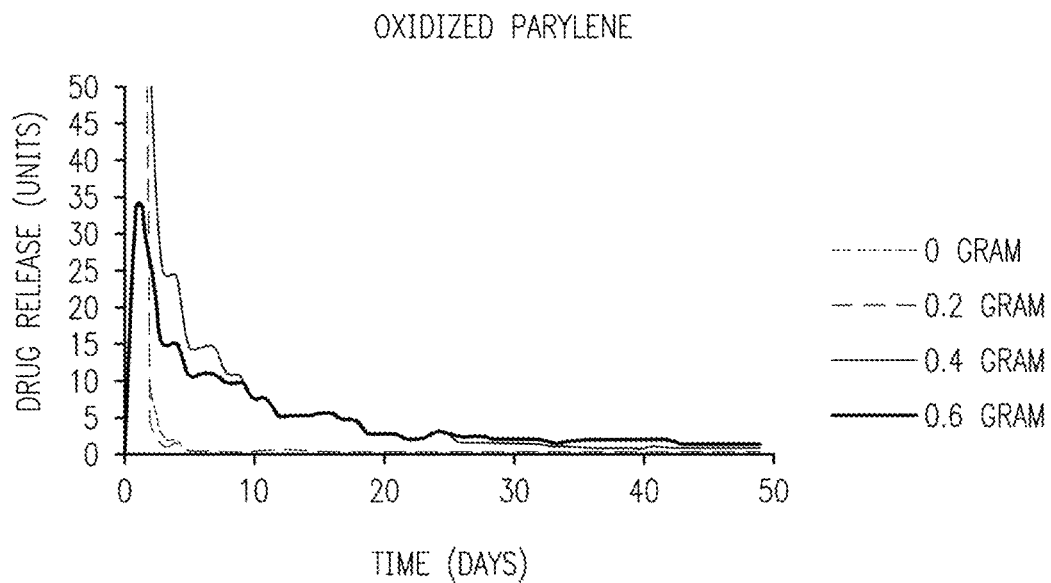
FIG. 6D is a graph showing the average dexamethasone release per day from the devices graphed in FIG. 6C.
Figure 6E:
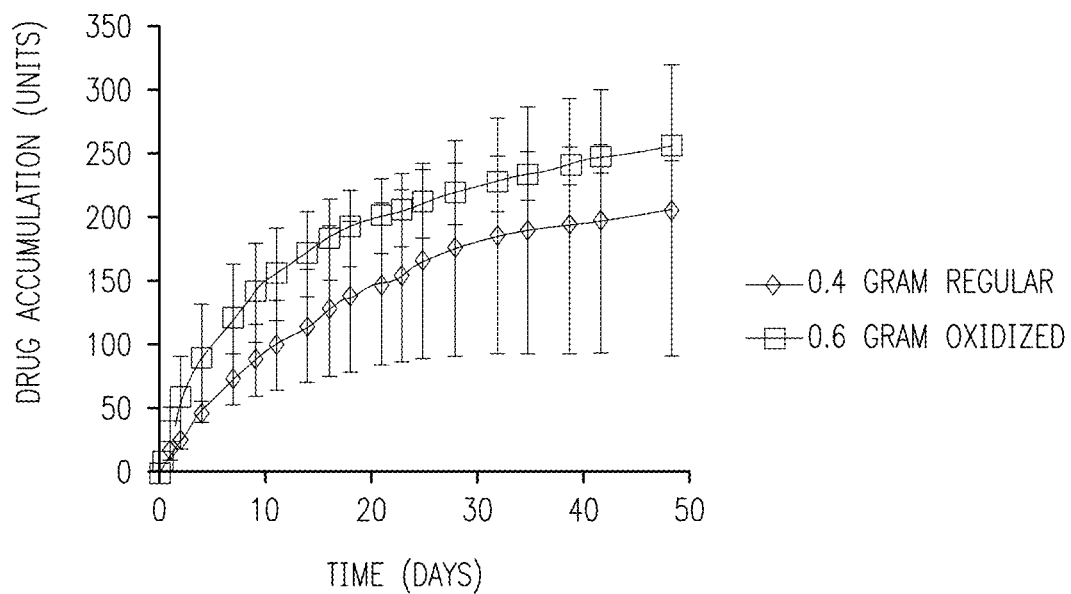
FIG. 6E is a superimposition of a similar dexamethasone elution profiles achieved by a first device having regular parylene barrier microfilm and a second device having an oxidized parylene barrier microfilm according to the present invention where the barrier microfilms are of different thickness and FIG. 6F is a superimposition of the average dexamethasone release per day from the devices graphed in FIG. 6E.
Figure 6F:
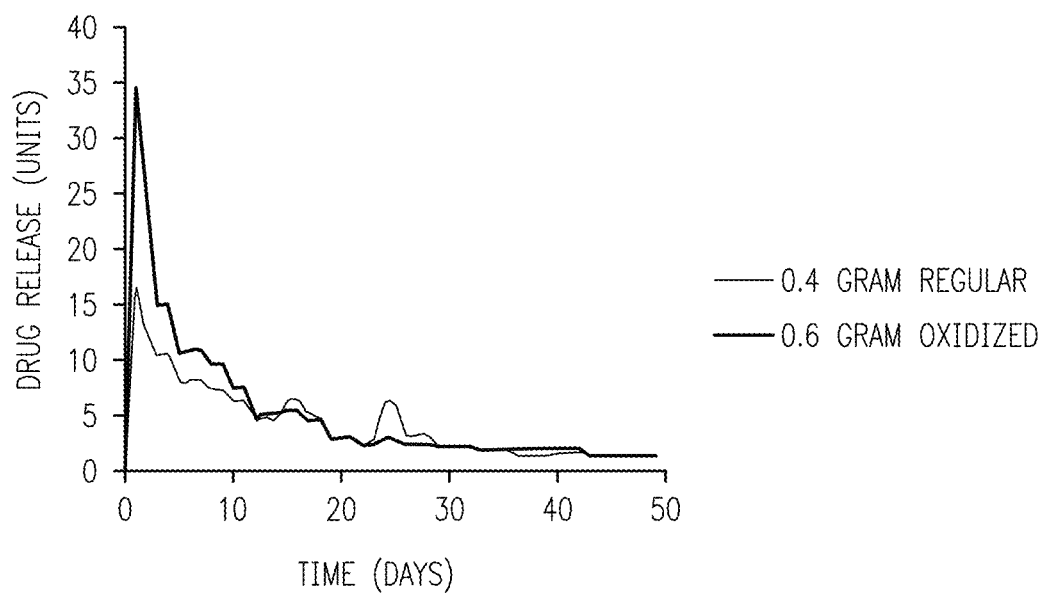

Referring to FIGS. 4 and 5 and Examples 1 and 2, it is theorized that a side or cross-sectional view of a microfilm of para-xylylene polymer not endowed with oxidatively functionalized para-xylene units with a therapeutic layer disposed about the microfilm would resemble a "mesa" with peaks and troughs in therapeutic density, as well as possibly peaks and troughs in the thickness of the construct. This is in turn could limit the breadth of therapeutics that can efficaciously permeate the para-xylylene polymer microfilm and/or result in sporadic drug elution. If a top layer (i.e., in simplicity, an overlying porous barrier microfilm and further discussed below) is part of the construct, upon deformation, such a topography could result in delamination with massive therapeutic release. It could also result in certain perturbation of the top layer.

Continuing to refer to FIGS. 4 and 5 and Examples 1 and 2, in contrast, endowment of the microfilm of para-xylylene polymer with oxidatively functionalized para-xylene units significantly reduces the pronounced sharp features of the therapeutic residue to promote a more uniform therapeutic permeation and spread, as well as possibly a more uniform thickness of the construct. This in turn could promote the breadth of therapeutics that can efficaciously permeate the microlayer and/or lead to a more controlled and accurate therapeutic elution. If a top layer (i.e., in simplicity, an overlying porous barrier microfilm and further discussed below) is part of the construct, this could also promote a more robust device less prone to delamination. It could also promote a more robust top layer.

It is further believed that oxidatively functionalized para-xylene units makes para-xylylene polymer more hydrophilic. This in turn can effect the interaction of the para-xylylene polymer with water and physiological fluids. It also can effect the interaction of the para-xylylene polymer with a therapeutic which may for example, be hydrophilic. This is an additional theory to explain the unexpected results and enhanced performance of para-xylylene polymer endowed with oxidatively functionalized para-xylene units.

The coupling of the processing steps of fabricating a base layer and top layer to form a bilayer microfilm (it is noted that the bilayer microfilm is integrated with a therapeutic layer) with the additional processing step of endowment of the microfilm of para-xylylene polymer with oxidatively functionalized para-xylene units is describable as a tunable functionalization with a gas-based wetting enhancement/architectural preservation agent using a high temperature conjugation system. The oxidation functionalization serves as a foundation to call the bilayer a dynamic material, while regular parylene and all of its derivatives that are not oxidized are steady state/inert compounds.

In certain applications and environments, the more comprehensive spreading of the therapeutic that occurs with the enhanced "wettability" correlates with extended release such that it can be used to increased release duration. Endowment of the microfilm of para-xylylene polymer with oxidatively functionalized para-xylene units diffuses the therapeutic in the parylene to alleviate clumping and density build up. This in turn translates to significantly change elution characteristics to achieve more accurate delivery.

Referring to FIG. 6 and Example 3, the deployment of oxidized parylene can afford an increase in thickness of a microfilm while maintaining the elution profile of a thinner regular parylene microfilm. This in turn can translate into an increase in strength, resistance to tearing and stability. In Example 3, a 0.6 gram microfilm of oxidized parylene has about the same elution profile of Dexamethasone-Fluorescein as does the 0.4 gram layer of unoxidized parylene. Thus, applying oxidation to a parylene microlayer can be used to enhance the tear resistance of a standalone controlled elution device that is flexible, undergoes deformation and is subject to tearing. In certain applications and environments, tear resistance may be advantageous and thus desirable to have a device that is thicker with the same elution profile as a thinner device that is weaker and less stable.

Changing subject to another technological advancement by the present invention, the architecture of controlled elution devices according to the present invention can employ multilayering of pary-xylene in a microfilm. The multilayered pary-xylene microfilm can be employed in a top or barrier layer that functions as a regulator. It can be employed in a base layer that functions, inter alia, as a reservoir and/or regulator. As discussed in more detail below, multilayered pary-xylene microfilm is fabricated by repeat chemical vapor deposition.

Referring to FIGS. 7 and 8 and Examples 4 and 5, manipulating the number of layers in a multilayer and adjusting the thickness of those layers can be used to tune the elution profile of a therapeutic to achieve a desired elution profile and/or more accurately control the elution of a therapeutic. Referring to FIG. 7 and Example 4, where a multilayer serves as a top or barrier layer to regulate elution, there can be a nonlinear relationship between elution and the number of layers in the multilayer. Further, depending on the size of therapeutic, its polar and/or ionic character and other factors, the relationship between elution and the number and thickness of the layers in a microfilm comprised of a plurality of distinct laminate layers could be a parabolic, hyperbolic, a combination of the two with an inversion point, linear or some other relationship. In utilizing this invention, a non-laborious experiment like that in Example 6 can be run to determine the relationship.

Refer to FIG. 8 and Example 5, manipulating the number of layers in a multilayer and adjusting the thickness of those layers can be used to enhance the mechanical stability of a standalone controlled elution device that is flexible, undergoes deformation and is subject to tearing. In certain applications and environments, to enhance mechanical stability it may be advantageous to have a device that is thicker that has the same elution profile as a thinner device. In other applications and environments, to enhance mechanical stability it may be advantageous to have a device that is thinner that has the same elution profile as a thicker device. Referring to Example 4, a thinner multilayer laminate microfilm can provide approximately the same elution profile as a thicker mono-layer microfilm.

Referring to all of the Examples, a broad spectrum of classes of therapeutics can be integrated in devices according to the present invention. As discussed below, in embodiments of the present invention the therapeutic is deposited. The deposited therapeutic can be physically, ionically, or covalently linked to the deposited surface. The amount of therapeutic deposited is a parameter that can affect elution profile of time extended delivery, as well as the amount of therapeutic released.

Embodiments of this invention can be integrated with therapeutics ranging from small molecules of molecular weight at least as low as few atomic mass units up to large proteins like IgG having a molecular at least as great as 150 KiloDaltons and comprised of multiple protein chains. Embodiments of this invention can integrated with therapeutics of all different hydrophobicities ranging from highly hydrophilic to highly hydrophobic like dexamethasone and steroid class therapeutics. In figurative terms, hydrophobic and aromatic molecules do not get trapped or stuck in the pores of porous parylene. Embodiments of this invention can integrated with high value therapeutics such as Interferon-alpha2b.

To accommodate a particular therapeutic or combination of therapeutics, it may advantageous to tune an embodiment of this invention so as accommodate the therapeutic(s) or class(es) of therapeutics. To accommodate a particular therapeutic or combination of therapeutics, the device can be tuned, inter alia, by using a monolayer microfilm that is oxidized and/or a multilayer microfilm varying the number layers, thickness and oxidation of the plurality of distinct laminated layers of the multilayer. In a broader sense, the variables are tuned in the context of achieving a desired elution profile and/or mechanical stability.

The classes of therapeutics that can be integrated into embodiments of the present invention include biologics, biosimilars, thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, inhibitors, free radical scavengers, chelators, antioxidants, anti polymerases, antiviral agents, photodynamic therapy agents, and gene therapy agents.

The classes of therapeutics that can be integrated in devices according to the present invention also include small molecules, proteins, multiprotein macromolecules (i.e. antibodies), nucleic acids (including, but not limited to, siRNA, shRNA, miRNA, etc.), macromolecules consisting of protein-nucleic acid complexes.

The therapeutics that can be integrated in devices according to the present invention include therapeutics selected from the group consisting of hydrophilic small molecule drugs, hydrophobic small molecule drugs, steroidal small molecule drugs, macrocyclic small molecule drugs, small molecule drugs without bulky side groups, small molecule drugs with bulky side groups, small molecule drugs in pharmaceutical acceptable salt forms, peptide biologics, protein biologics, multi-chain protein biologics, glycosylated protein biologics, immunoglobulins, micro chain nucleic acid biologics, short chain nucleic acid biologics, nucleic acid biologics, aptamer biologics, protein-nucleic acid complex biologics, lipid biologics, lyposome biologics and PEGylated forms of any of the foregoing.

The therapeutics that can be integrated in devices according to the present invention include therapeutics selected from the group consisting of dexamethasone, doxorubicin, IgG, interferonα2b, mitomycin and paclitaxel.

The therapeutics that can be integrated in devices according to the present invention include therapeutics selected from the group consisting of hormones, hormone mimetics and hormone derivatives, including plant hormones.

Having discussed elements of the present invention, with more disclosure and a discussion on making below, the discourse will now go to a discussion of architecture of devices. Notwithstanding, before moving to a discussion of architecture, it is pointed out that the above described theories are believed to explain the strong extended release results and enhanced mechanical stability of a para-xylylene polymer device endowed with oxidatively functionalized para-xylene units. Notwithstanding, the invention claimed is not bound to any theory, or the correctness of that theory, to explain what is occurring.

Figure 9A:
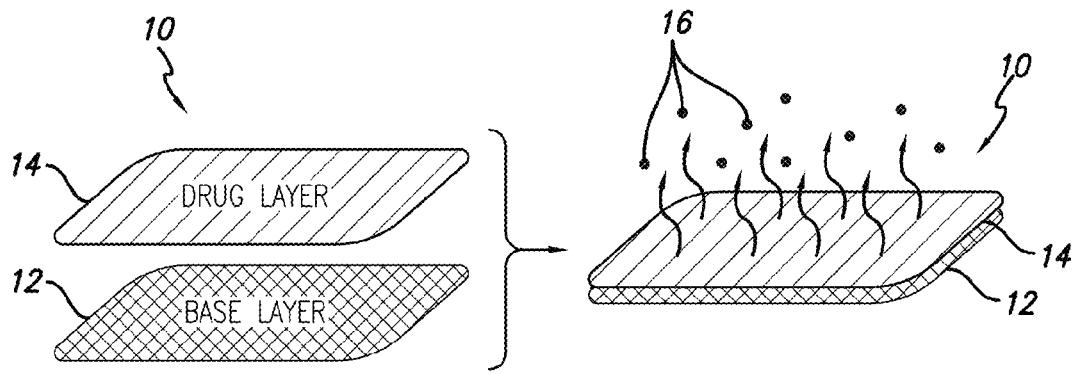
FIGS. 9A, B, C, D, E and F are schematic illustrations of standalone controlled elution devices according to the present invention.

Referring to FIG. 9A, one alternative embodiment of the present invention is bilayer unidirectional device (10). The architecture of this alternative embodiment is a base or first layer that is usually non-porous (12). One or more therapeutic(s) (16) are deposited on the base (12) to form a therapeutic layer or reservoir (14). Therapeutic(s) (16) typically elutes from one side of the device.

Figure 9B:
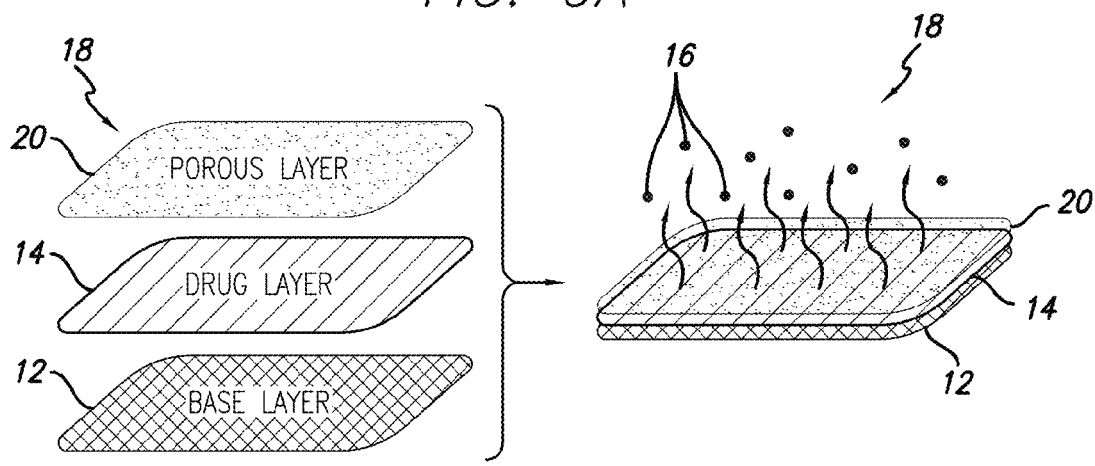

Referring to FIG. 9B, one alternative embodiment of the present invention is a trilayer unidirectional device (18) with a porous monofilm regulating or barrier layer (20). The architecture of this alternative embodiment is a base or first layer that is usually non-porous (12). One or more therapeutic(s) (16) are deposited on the base (12) to form a therapeutic layer or reservoir (14). The therapeutic layer or reservoir (14) is over laid with a porous monofilm regulating or barrier layer (20) and hence a trilayer is formed. Therapeutic(s) (16) typically elutes from one side of the device.

Figure 9C:
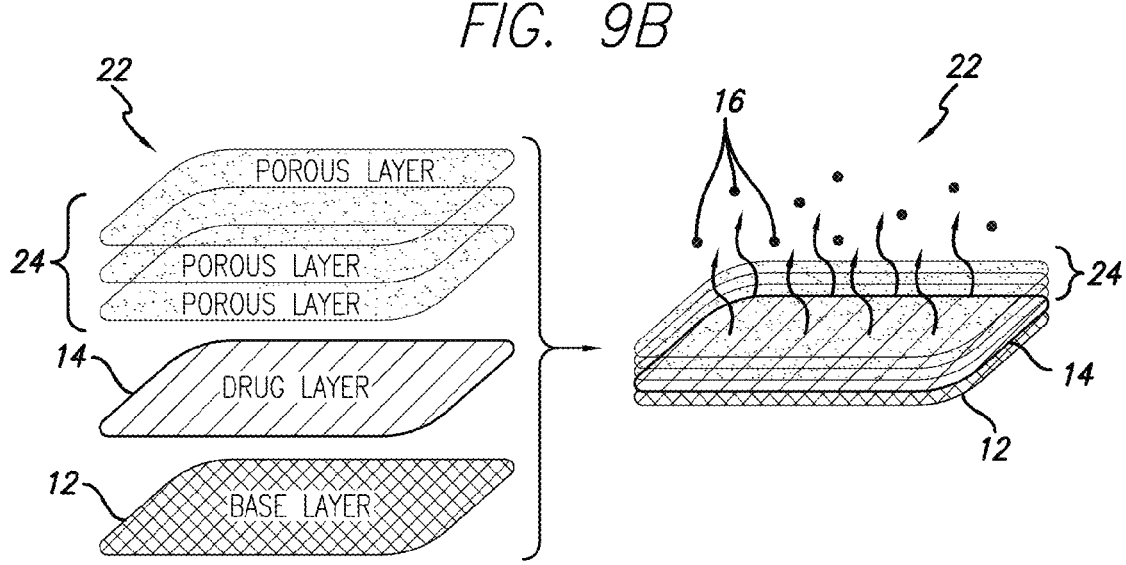

Referring to FIG. 9C, one alternative embodiment of the present invention is a trilayer unidirectional device with a multi-layer laminate as a barrier layer (22). The architecture of this alternative embodiment is a base or first layer that is usually non-porous (12). One or more therapeutic(s) (16) are deposited on the base (12) to form a therapeutic layer or reservoir (14). The therapeutic layer over laid with a regulating or barrier layer that is a multi-layer laminate (24) and hence a tri-layer architecture. Therapeutic(s) (16) typically elutes from one side of the device.

Figure 9D:
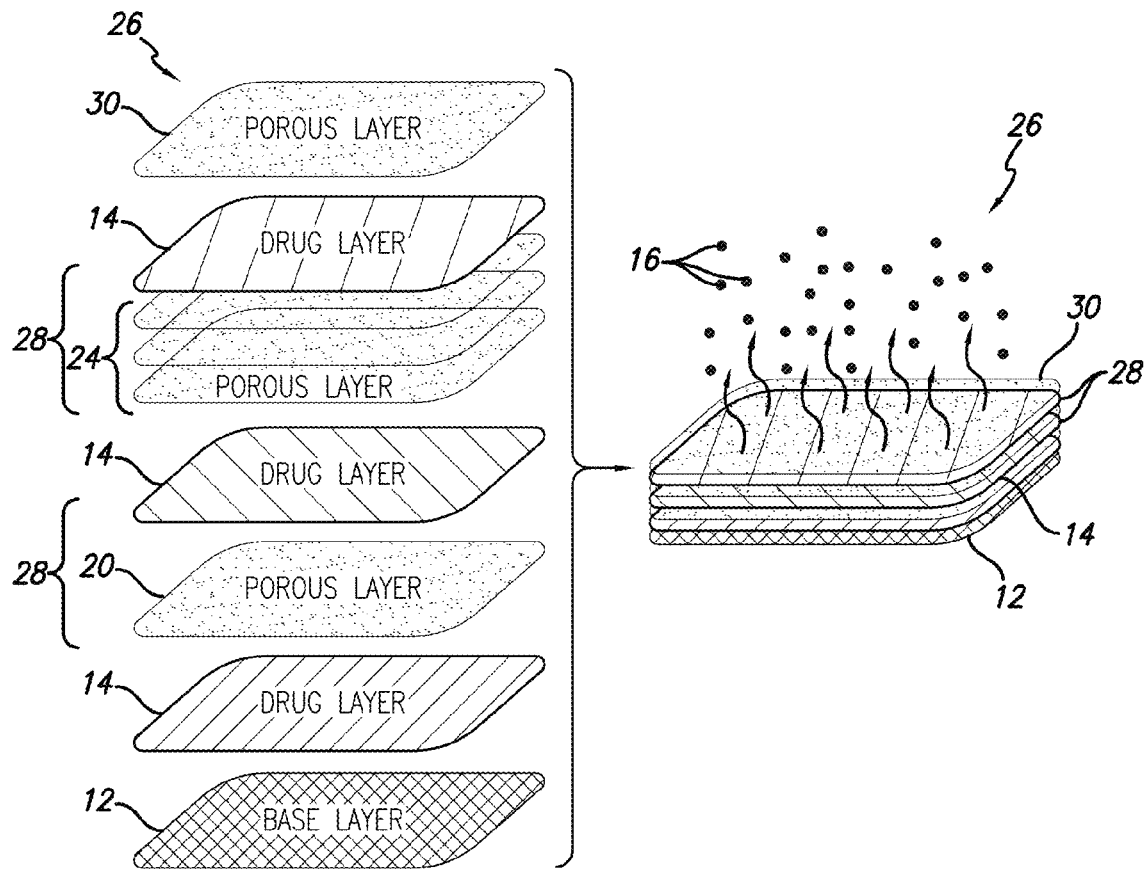

Referring to FIG. 9D, one alternative embodiment of the present invention is a plurality of bilayers for unidirectional release (26) of therapeutic(s) (16). The architecture of this alternative embodiment is a base or first layer that is usually non-porous (12). Overlying this base (12) is a first therapeutic layer or reservoir (14) comprised of a deposit of one or more therapeutics (16). Overlying this first therapeutic layer (16) is a plurality of bilayers (28) comprised of either a porous monofilm that is a regulating or barrier layer (20) or a porous multilayer laminate (24) that is a regulating or barrier layer with a therapeutic(s) (16) deposited thereon to form a therapeutic layer or reservoir (14). Optionally, an overlying top or barrier layer that is porous comprised of either a porous monofilm that is a regulating or barrier layer or a porous multi-layer laminate that is a regulating or barrier layer (30). Hence, a plurality of bilayers (28) stacked or laminated one on top of another. This device allows for more elaborate elution profiles of a therapeutic or combination of therapeutics (16) where the type and quantity of therapeutic (16) can be varied in each bilayer (28) and/or first therapeutic layer (16).

Figure 9E:
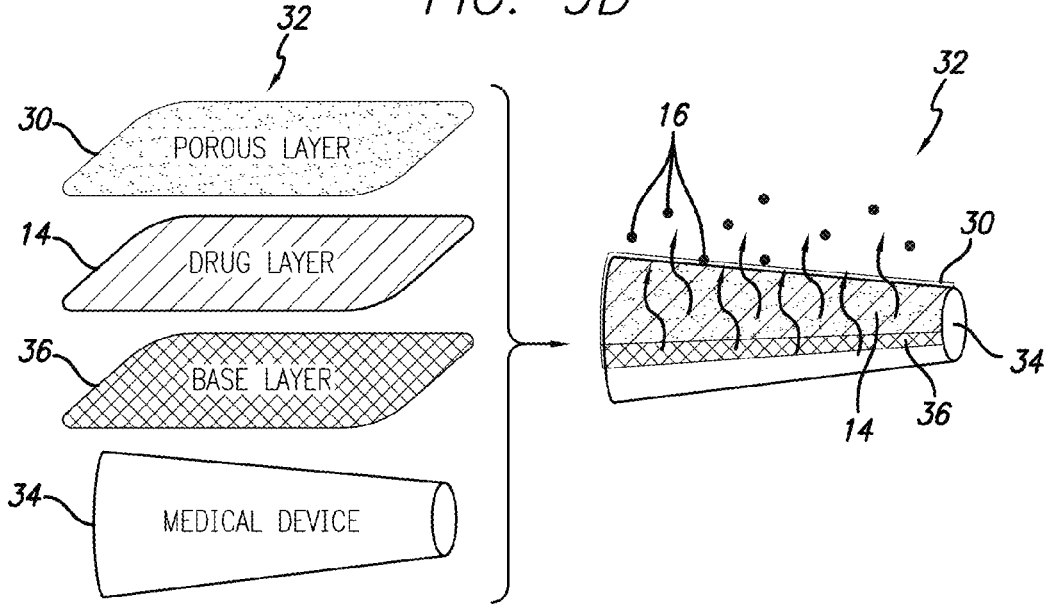

Referring to FIG. 9E, one alternative embodiment of the present invention is a controlled elution device that is the controlled elution component of a medical device (32). Typically, this device (32) is for the unidirectional release of therapeutic(s) (16) in connection with the surface of a medical device (34). An architecture of this alternative embodiment is a first or base layer (36) disposed about a surface of the medical device (34). This first or base layer (36) need not be parylene. One or more therapeutic(s) (16) are deposited on the first or base layer (36) to form a therapeutic layer or reservoir (14). There is an overlying regulating layer that is a monofilm (20) or multi-layer laminate (24). Optionally, there can be a plurality of bilayers on top the previously described barrier or regulator layer (not illustrated in FIG. 9E and see FIG. 9D.)

Figure 9F:
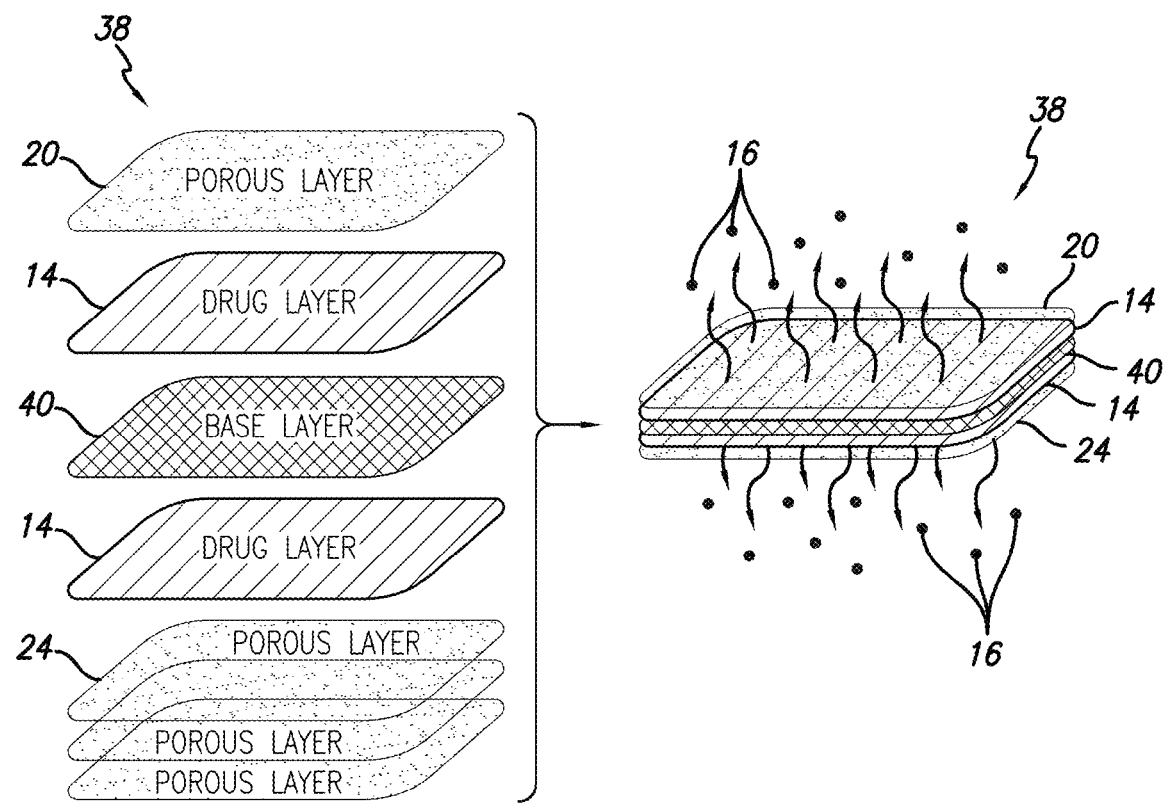

Referring to FIG. 9F, one alternative embodiment of the present invention is a bidirectional device (38) for the two directional elution of therapeutic(s) (16). An architecture of this alternative embodiment is a central base microfilm (40) having a first and second side. A first layer of therapeutic or combination of therapeutics (16) is disposed on the first side of the central microfilm (40) to form a therapeutic layer or reservoir (14). Disposed on this first layer of therapeutic is a first barrier microfilm (20) that is porous parylene which regulates elution comprised of either a porous monofilm that is a regulating or barrier layer (illustrated) or a porous multi-layer laminate that is a regulating or barrier layer (not illustrated.) A second layer of therapeutic or combination of therapeutics (16) is disposed on the second side of the central microfilm (40) to form a therapeutic layer or reservoir (14). Disposed on this second layer of therapeutic (14) is a second barrier microfilm (24) that is porous parylene which regulates elution comprised of either a porous monofilm that is a regulating or barrier layer (not illustrated) or a porous multi-layer laminate that is a regulating or barrier layer (illustrated.).

Figure 10A:
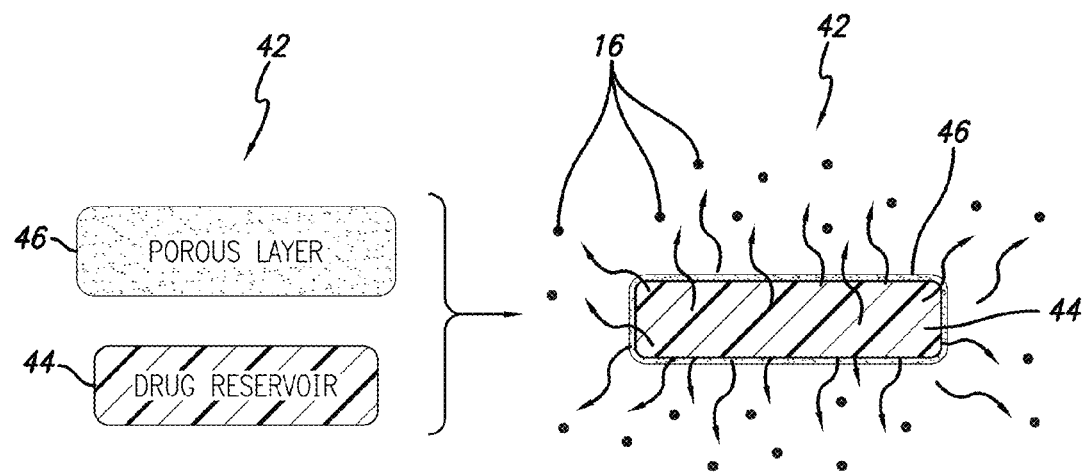
FIGS. 10A and B are schematic illustrations of standalone controlled elution devices according to the present invention.

Referring to FIG. 10A, one alternative embodiment of the present invention a device that is a microfilm encapsulation of a reservoir of therapeutic or combination of therapeutics (42). There is reservoir of a therapeutic or combination of therapeutics (44). This reservoir (44) is encapsulated by an encapsulating microfilm can be a multilayer of regular parylene (not illustrated,) a monolayer of oxidized parylene (46) (illustrated) or a multilayer having oxidized parylene in at least one of the layers of the multilayer (not illustrated). The reservoir (44) can be a conventional pill. The encapsulation microfilm regulates elution of the therapeutic(s) (16).

Figure 10B:
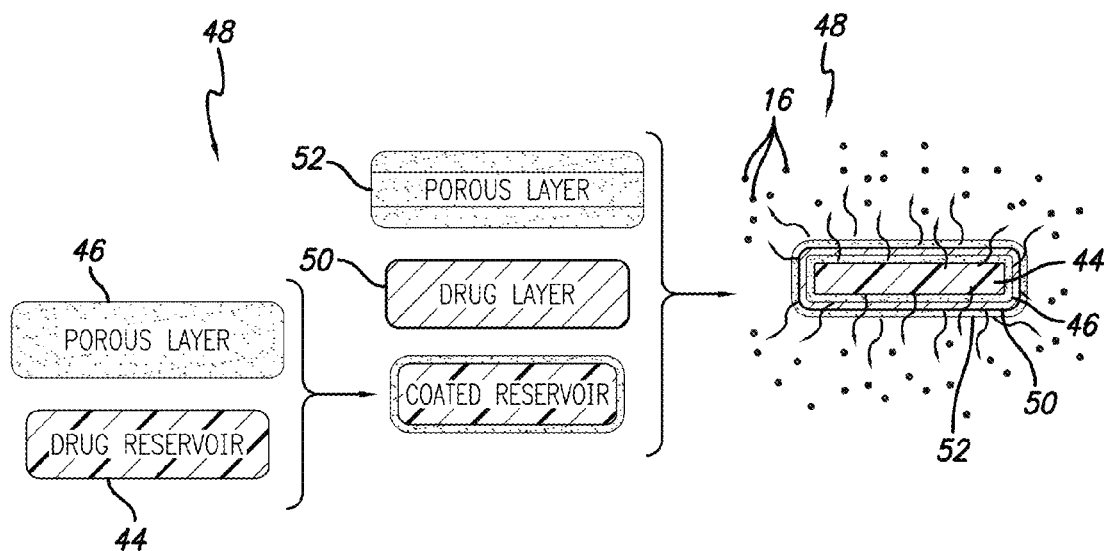

Referring to FIG. 10B, one alternative embodiment of the present invention has an architecture that is a device that is a microfilm encapsulation of a reservoir of therapeutic or combination of therapeutics and surrounding this first encapsulation microfilm, there are one or more of bilayers a drug layer and porous microfilm layer (48). The reservoir (44) and drug layer(s) (50) can be a therapeutic or combination of therapeutics. The microfilms (46, 52) can be a multilayer of regular parylene (52) (illustrated), a monolayer of regular or oxidized parylene (46) (illustrated) or a multilayer having oxidized parylene in at least one of the layers of the multilayer (52) (also illustrated under the same reference numeral, 52). The reservoir (44) can be a conventional pill. The microfilms (46, 52) regulates elution of the therapeutic(s) (16).

The preferred thickness of a standalone controlled elution device is between about 10 microns to about 200 microns; however, thinner devices can be more preferred. A preferred multilayer is a laminate of 2 to 4 layers. A more preferred thickness of a standalone controlled elution device is between 5 nanometers to about 5000 nanometers. A most preferred thickness of a standalone controlled elution device is between 5 nanometers to about 500 nanometers.

At this point, the discussion turns to a discourse on how to construct devices. For the purposes of enablement, and not for the purposes of defining terms, the journal article and patents referenced in the background section of this patent are incorporated herein by reference. In addition, for the purposes of enablement, and not for the purposes of defining terms, any patents or other references listed in an information disclosure statement(s) filed during the prosecution of the application matriculating into this patent are incorporated herein by reference.

Devices can be fabricated upon a solid surface (substrate) as a temporary platform which can be eventually removed for standalone activity. This solid surface can be a glass slide, coverslip, silicon wafer, plastic disc and the like.

Onto to this solid surface, a base layer of para-xylylene polymer is deposited. This can be done via a room temperature chemical vapor deposition process. In the chemical vapor deposition process, it is believed that para-xylene monomer is sprayed as a monolayer onto the solid surface, that said monomer reversibly attaches to the solid surface and self polymerizes. The result being a wafer of para-xylylene is created by deposition onto the solid surface.

By way of example, and not by way of limitation, a Specialty Coating Systems Lab Coater 2 (model PDS 2010, SCS Coatings, Indianapolis, Ind.) per the manufacturer's protocol can be used to deposit a base layer of parylene C onto a glass disc via a room temperature chemical vapor deposition.

A layer can be either nonporous or porous depending on the thickness of the para-xylylene polymer deposition. Typically, if the base layer is equal to or greater than about five microns the base is nonporous and conversely if the base layer is equal to or less than about one micron the base is porous.

The oxidative processing of parylene typically substitutes an —OH, —COOH, —COO—, —C=O, or —CO— unto the benzene ring at the position of Hydrogen or other moiety and may involve a substitution at the Cl— or other moiety by which the parylene was derivatized. Oxidation that involves substitution of the Cl— is generally less preferred. Alternatively, the oxidative process breaks the benzene ring to yield an —OH, —COOH, —COO—, —C=O, or —CO— group on the broken ring. The oxidative process encompasses the several known processes by which to oxidize parylene, is not limited to any one process, and further encompasses processes that may developed in the future.

Oxidative functionalization may be accomplished by ultraviolet light, a plasma cleaner, chemically driven oxidization or any other oxidation processing of the para]xylylene.

In oxidizing by a plasma cleaner, a plasma cleaner means converts air into a plasma species (ion or radical) and this plasma species is shot over the surface of the para-xylylene polymer layer. In addition to oxidization, the treatment of parylene with this plasma both cleans its surface through ablation, the mechanical elimination of contaminants from the polymer surface, sterilizes the parylene surface by killing most infectious agents (i.e. bacteria, fungus, etc.)

Ultraviolet oxidation involves bombarding the parylene surface with UV light. The UV light produces radical species (i.e. hydroxyls from water or hydrogen peroxide in the oxidation chamber) which are then incorporated onto the parylene surface. Ultraviolet oxidation also has the added benefit of sterilizing the parylene surface by killing most infectious agents (i.e. bacteria, fungus, etc.)

Chemically driven oxidation involves treating the parylene surface with a chemical oxidant, for example hydrogen peroxide or permanganate. The chemical oxidant facilitates the addition of oxidative species to the parylene surface. Chemically driven oxidation also has the added benefit of sterilizing the parylene surface by killing most infectious agents (i.e. bacteria, fungus, etc.).

The preferred way to oxidatively functionalize is using a plasma driven process. This activates the parylene surface via oxidation, the addition of hydroxyl, carboxyl and/or carbonyl groups to the surface of the parylene. Thus there is a deposit of an atomic layer of wetting-enabling oxygen to support the comprehensive spreading of the drug/therapeutic.

Onto to a layer, a therapeutic is disposed about, permeated in and/or deposited. This therapeutic addition step forms a reservoir of therapeutic for elution. The therapeutic may be physically, ionically, or covalently linked to the surface of the layer. Though the potential exists to harness therapeutics via ionic or covalent linkages, the uncertainty of the kinetics of therapeutic release makes these options less preferred.

A preferred method to dispose about, permeate and/or deposit the therapeutic on or to a layer is a spotting followed by evaporation. In this method, a solvent containing the therapeutic is deposited on the layer. The solvent than evaporates off solvent slowly. As solvent evaporates off, the therapeutic falls down and depending upon the wettability of the layer, the deposited therapeutic diffuses in the layer. This leaves a dry therapeutic that is permeated in and/or disposed about the surface of the layer and forms a reservoir of therapeutic.

Following the therapeutic addition step, zero or more overlying layers of porous layers of pary-xylene can be deposited. This is done as previously described.

A plurality of distinct laminated layers or multilayer can be deposited by repeating the above process. In subsequent chemical vapor depositions, the para-xylene monomer is sprayed onto an underlying layer of polymerized para-xylylene. Similar to when the monomer is sprayed on the solid surface, it self polymerizes. Unlike when the monomer is sprayed on the solid surface, when sprayed on an underlying layer of polymerized para-xylylene, it essentially irreversibly attaches to form a laminate. This process is repeated as many times to build up the number of desired layers. In between repeating the deposition process, an oxidative functionalization process can be performed (see, discussion above.)

For a plurality of bilayers, the previously described procedures are repeated.

The completed devices are then removed from the substrate via dicing. For device removal, the desired shape can either be conferred to the device via the substrate dimensions or the shape can be cut to the desired final parameters from off of the substrate. In either case, the dimensions of the parylene film can be first cut with a scalpel, then carefully peeled off of the substrate foundation, leaving the intact parylene film device.

The para-xylylene polymer can be formed into envelope that encapsulates a reservoir by the following procedure. Two microfilms can be stacked or a microfilm can folder over on an approximately a center line. All but one of the sides can be closed and sealed by solvent or heat welding or adhesive. A therapeutic or combination of therapeutics is loaded into the envelope and the remaining open side is closed or sealed in the foregoing manner.

Embodiments of the present invention can be in connection with a medical device as is taught in the art in the Cook and Microport patents, see, supra. The base or first layer adjacent to the medical device can be parylene or another material.

To tune a controlled elution device, parameters are manipulated and adjusted to achieve a desired elution of a therapeutic or combination of therapeutics, as well as mechanical stability. For example a gradual release followed by a burst (or snap release) followed by a constant (or flat) release. The typical parameters used in tuning are:
  selecting uni-directional, bidirectional or encapsulation architecture;
  selecting a plurality of bi-layer, tri-layer or plurality of bi-layer architecture;
  selecting a monolayer or multilayer architecture;
  Selecting oxidative wetting for a microfilm or layer
  adjusting the number of microfilms or layers;
  adjusting the thicknesses of a microfilm or a layer;
  adjusting the quantity of therapeutic deposited and
  manipulating the overall size of the device.

Referring to the Examples below, to tune these parameters a series of time elution experiments can be performed to determine relationships of the parameters for a particular therapeutic or combination of therapeutics and optimizing those parameters. By way of illustration, and not by way of limitation, a first experiment is conducted testing elution as function of the number of layers in a multilayer. Next an experiment is run testing elution as a function of thickness. Next an experiment is run testing elution as a function of oxidation. From these experiments it is deduced putative architecture to yield the desired profile. Test devices are constructed and the ones that best fit the profile are selected. These devices than are subjected to mechanical stability testing by shaking, tearing and deforming. A Candidate device is chosen. In the alternative, a default architecture as described herein can be employed.

The typical mode of action is a solvent in flow through an exterior layer of the device. The solvent can be naturally present physiological fluid or a specially applied fluid or gel such as phosphate buffer saline. The solvent influx solvates a dry therapeutic. This results in an outflow of therapeutic.

In more detail, internal and wound applications generally are to moist surface and do not require an exogenous fluid or gel for solvent exchange. Were the device is attached to a dry surface, there preferably is an exogenous fluid or gel for solvent exchange.

INDUSTRIAL APPLICABILITY

Embodiments for the present invention are intended for the administration of a therapeutic to life forms. Preferably, the life form is a plant, veterinary animal or a human. More preferably, the life form is a veterinary animal or a human.

Embodiments of the present invention are intended to serve as a biostable, standalone platform that is capable of sustaining localized or systemic release while maintaining the device presence in one location dependent upon the location of implantation.

Embodiments of the present invention are intended for sub-cutaneous implantation or on ]organ deposition. Embodiments of the present invention are for deposition against the skin for external use for the ex vivo administration of a therapeutic or combination therapeutic. Such embodiments can be worn against the skin. A preferred location for external use is worn under arm in an arm pit for transdermal administration. Other potential routes of delivery that are correlated to both localized and systemic activity are within the scope of the invention.

Embodiments can be used for wound care. An application is care of diabetic lesions that could result in amputations. Embodiments of the present invention can be used for the treatment of cancer, inflammatory suppression, anti-viral applications, wound healing, scar formation suppression, nutrient delivery, pain management and the like.

Embodiments of the present invention can be used as the controlled elution component of ocular implants for ophthalmic drug delivery for the treatment of disorders including, inter alia, macular degeneration, diabetic retinopathy and other ophthalmic maladies. Typically, the ocular drug-delivery implant would be implanted in the eye and left in place until the drug is fully dispensed and then removed.

Embodiments of the present invention can be used as the controlled elution component of a dental patch.

Embodiments of the present invention can be used for the delivery of hormone adjunct or replacement therapy and be correlated to both localized and/or systemic activity.

Embodiments of the invention can be used in connection with medical devices in which they are deployed as the controlled elution component of said devices. Such medical devices include stents. In addition, such devices include neurostimulation devices, anastomosis devices, hearing-assist devices, birth control occlusion devices, spinal repair devices, diabetic devices, dental implants (in addition to a dental patch, supra,) breast implants, pacemaker and electrostimulation leads and joint replacements.

The previously described versions of the present invention have many advantages. One advantage of versions of this invention is that oxidation significantly reduces the pronounced sharp features of a therapeutic that resides on and/or permeates a para-xylylene polymer microfilm so as to enhance wetting for therapeutic deposition resulting in a more conformed and uniform density.

Another advantage of versions of this invention is a more uniform controlled release of the therapeutic due to a more uniform density of the loaded therapeutic in an oxidized parylene layer than with an unoxidized parylene layer.

Another advantage of versions of this invention is that the addition of oxygen species has the ability to extend therapeutic release and said extension can be clinically significant.

Another advantage of versions of the present invention is a multiparameter controlled elution device which can be tuned or for fine tuned to achieve a particular elution rate or profile.

Another advantage of versions of this invention is a standalone capable controlled elution device that can undergo deformation that is of a clinically usable size that has strength, resistance to tearing and stability. In succinct terms, "robust." Along the same lines, another advantage of versions of this invention is a controlled release device that is not supported on a medical device; that is, that the coatings are not against a solid backing.

Another advantage of versions of the present invention is a small nano-scale to micro-scale device suitable for in vivo and ex vivo clinical applications for the extended delivery of therapeutics or combination of therapeutics than could not be previously be time delivered in a clinically meaningful way.

Along similar lines, another advantage of versions of the present invention is to provide controlled elution of a wide range of therapeutics that can potentially alleviate or cure serious diseases and infections for which delivery by current means results in serious side effects and/or limited time-dose delivery that in turn limits their effectiveness.

Another advantage of versions of the present invention is to provide clinicians with a controlled elution device that can limit the number of treatments a patient requires for complex, highly toxic therapeutics.

Another advantage of versions of the present invention is cost effectiveness; that is, versions of the present invention provide a low-cost, customizable microfilm therapeutic delivery systems.

Overall, an advantage of versions of the present invention is to improve the quality of life of individuals who are afflicted with poor health.

EXAMPLES

The following examples further describe and demonstrate embodiments within the scope of the present invention. The examples are given solely for the purpose of illustration and are not to be construed as limitations or restrictions of the present invention, as persons skilled in the art will quickly realize many variations thereof are possible that are all within the spirit and scope of the invention.

Example 1

Referring to FIG. 4, Example 1 is an experiment to compare therapeutic spreading with respect to an unoxidized parylene layer and an oxidized parylene layer. The therapeutic analyte was Doxorubicin-HCl. Doxorubicin-HCl is the salt version of the anti-cancer chemotherapeutic Doxorubicin: (8S,10S)-8-acetyl-10-[(2S,4S,5S,6S)-4-amino-5-hydroxy-6-methyl-oxan-2-yl]oxy-6,8,11,14-tetrahydroxy-1-methoxy-9,10-dihydro-7H-tetracene-5,12-dione, having four fused six member rings of which two are unsaturated and one is a dione and a pendant sugar group The Doxorubicin-HCl has a red color and is easily visualized with no additional modification.

Therapeutic addition to the parylene layer was accomplished via desiccation of 25 μl (microliters) of a 2 mg/ml (milligrams per milliliter) solution (50 μg (micrograms) total) Doxorubicin-HCl (Alexis Biochemistry, San Diego, Calif.) under a laminar flow hood.

FIG. 4 shows for two replicates a clear variation in therapeutic spreading. The stained area for oxidized parylene has about twice the radius or four times the surface area as that for unoxidized parylene. FIG. 5 is plot of therapeutic intensity vs. distance a from the a peripheral margin along a great diameter. Discarding values at the margin, for unoxidized paralyene there are two peaks and three troughs with amplitude variation ranging from about 0.009 to about 0.012 with units being arbitrary values of intensity measurement. In contrast, for oxidized paralyene, there are no significant peaks or troughs and near constant intensity at about 0.008.

Example 2

Referring to FIG. 5, Example 2 is an Atomic Force Microscopy (AFM) analysis of a para-xylylene polymer layer on a glass slide. In FIG. 5A, pertains to regular paralyene C and FIG. 5B pertains to oxidatively functionalized parylene C. Plotted along the x-axis is a distance in micrometers from a left margin of the layer. Plotted along the y axis is the up and down movement of the probe in picometers. The respective plots illustrate a more uniform layer with the oxidatively functionalized parylene C. The data indicates that the integrity of a parylene layer that is oxidized is about the same as that for a like thickness regular parylene layer. That is, a concern is alleviated that oxidation could result in gross morphological changes to the parylene layer.

Example 3

Referring to FIGS. 6A-F, Example 3 is an experiment to test the effect on drug elution of oxidizing parylene barrier microfilm relative to a device with a regular parylene barrier microfilm that is not oxidized. The analyte therapeutic was dexamethasone. Dexamethasone is a glucocorticosteroid. It has a trihydroxypregn-4-ene-3,20-dione as an unsaturated polycyclic core with unsaturated lower chain alkyl, fluoro and methyl substituents. Fluorescein was linked to the dexamethasone to monitor release.

Therapeutic addition to a base parylene layer of the device was accomplished via desiccation of 25 µl (microliters) of a 1.25 mg/ml (milligrams per milliliter) solution (31.25 µg (micrograms total) of Dexamethasone-fluorescein (source, Invitrogen Corporation, Carlsbad, Calif.) under a laminar flow hood. A first series of single layer regular parylene microfilms (not oxidized) having weights as a surrogate indicator of thickness of 0.2, 0.4 and 0.6 grams were deposited over dried dexamethasone-fluorescein drug, along with a control of no (0 grams) overlaying microfilm. A second series of single layer oxidized parylene microfilms having the weights were deposited over dried dexamethasone-fluorescein drug, along with a control.

Each of the devices was placed in 12 well plates in 1 milliliter of media as a solvent in conditions to mimic a physiological environment; i.e, DMEM Media (Thermo Scientific Hyclone Cell Culture & Bioprocessing, Logan Utah), 37 degrees Celsius, 5% carbon dioxide. The solvent was exchanged at the indicated time points and was monitored for released Dexamethasone-fluorescein using an fMax fluorimeter (Molecular Devices a division of MDS Analytical Technologies, Sunnyvale, Calif., excitation—485 nm (nanometers), emission—538 nm). The accumulation of released Dexamethasone-fluorescein was measured. All error bars are the standard deviations of the plotted data as calculated by three replicates of the experimental procedure.

The data demonstrate the capacity of a film comprised of only parylene to capture and release a drug in a controlled manner through a porous parylene layer. Release of the drug continues through 49 days. Increasing the amount of porous parylene layer decreases the amount of drug released and the rate of drug release. Oxidation of the porous parylene layer increases both the amount of drug released and the rate of drug release; e.g., the 0.6 gram layer of oxidized parylene has a different elution character than 0.6 gram layer that is unoxidized parylene and in particular, a greater elution. The 0.6 gram microfilm of oxidized parylene has about the same elution profile of Dexamethasone-Fluorescein as does the 0.4 gram layer of unoxidized parylene. This has the advantage of creating a thicker, and thus more durable, porous parylene layer for controlled drug release.

The data for 0.2 gram oxidized parylene coating can create some confusion. In this circumstance, all of the released dexamethasone-fluorescein is detected within the first 1-2 days, similar to what is seen with an uncovered bilayer device. However, with the 0.2 gram oxidized laminate device, the signal from the released drug is much lower (approximately 55%) than from released drug from an uncovered device. This is most likely an artefact created by the oxidation process where the plasma treatment of the 0.2 gram parylene laminate device cleans the drug from beneath the laminate layer, thus decreasing the detected signal from the released drug.

Example 4

Figure 7:
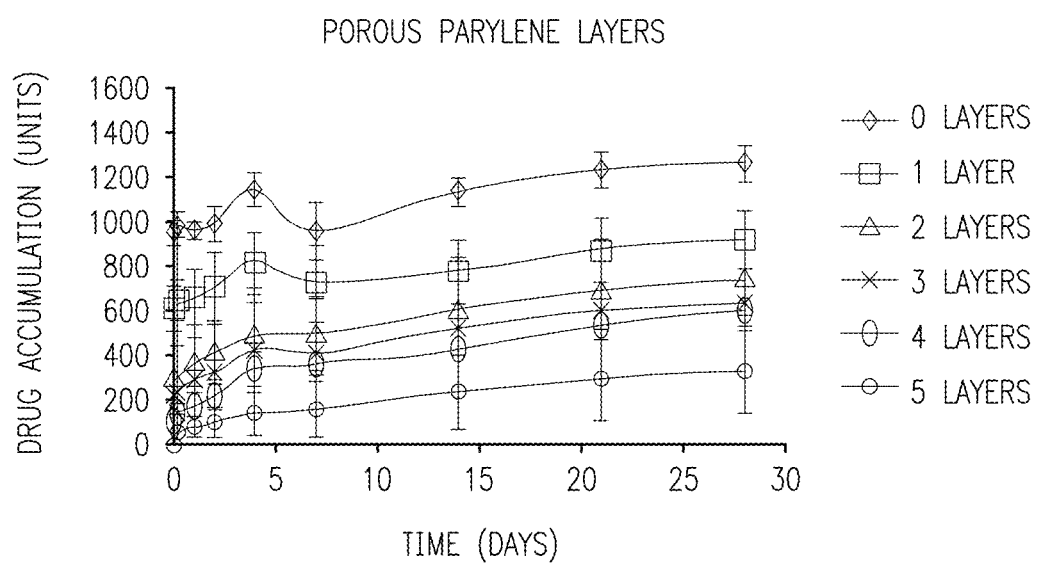
FIG. 7 is a graph showing the effect on dexamethasone-fluorescein elution of varying the number of layers in a parylene multilayer barrier microfilm according to the present invention.

Referring to FIG. 7, Example 4 is an experiment to test the effect on therapeutic elution of varying the number of distinct laminated layers in a para-xylyene polymer microfilm. As discussed above in Example 3, the target analyte is dexamethasone linked to fluorescein to monitor release.

A series of multilayer microfilms ranging from 1 to 5 layers of 0.1 grams of parylene were deposited over dried dexamethasone-fluorescein drug, along with a control of no (0 grams) overlaying microfilm. Each of the devices was placed in 12 well plates in 1 milliliter of media as a solvent in conditions to mimic a physiological environment: DMEM Media (Hyclone, supra), 37 degrees Celsius, 5% carbon dioxide. The solvent was exchanged at the indicated time points and was monitored for released Dexamethasone-fluorescein using an fMax fluorimeter (Molecular Devices, supra, excitation—485 nm (nanometers), emission—538 nm). All error bars are the standard deviations of the plotted data as calculated by three replicates of the experimental procedure. The accumulation of released Dexamethasone-fluorescein was measured.

The results indicate a stepwise, but nonlinear relationship between elution and the number of layers in the multilayer. With the elution for 0 grams of parylene being assigned a value of 1, the relative elution for 0.1, 0.2., 0.3, 0.4 and 0.5 grams of parylene is approximately 0.65, 0.5, 0.45, 0.4 and 0.1. The addition of increasing numbers of layers also decreases the initial "burst" release of drug from the film and creates a more linear elution from start to finish. This can be seen by comparing the elution profile from a device containing a single layer of 0.1 grams parylene with the elution profile from a device containing five layers of 0.1 grams parylene. These data demonstrate that adding multiple layers of porous parylene decreases the amount of drug released and the rate of this drug release, further "fine tuning" the release kinetics of a drug from a parylene film.

Example 5

Figure 8A:
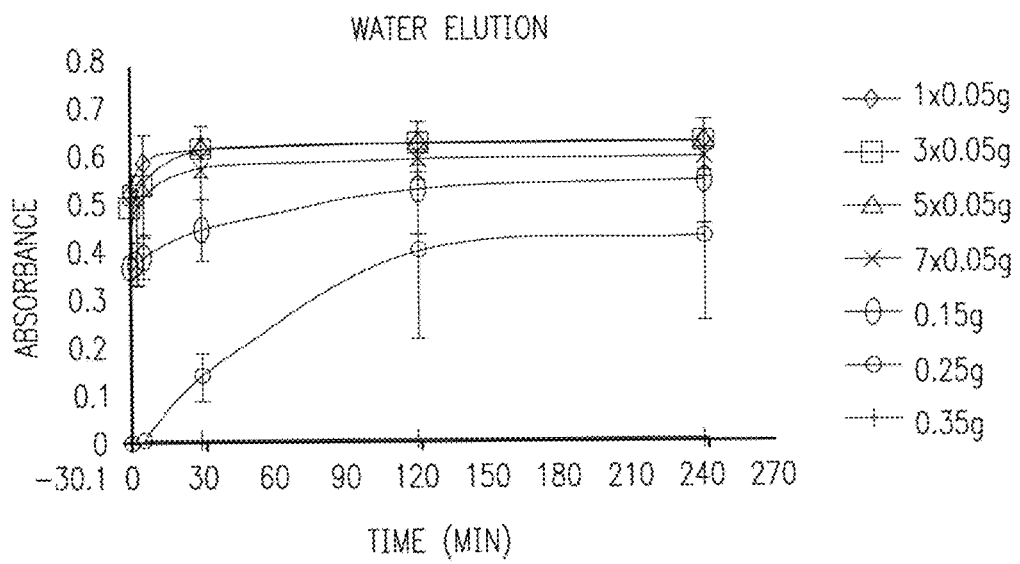
FIG. 8A are graphs of the accumulation of released Doxorubicin-HCl with water as a solvent from a multilayer parylene microfilm according to the present invention verses a comparable single layer microfilm as barrier layers and FIG. 8B are graphs of the accumulation of released Doxorubicin-HCl with media as a solvent from a multilayer parylene microfilm according to the present invention verses a comparable single layer microfilm as barrier layers.
Figure 8B:
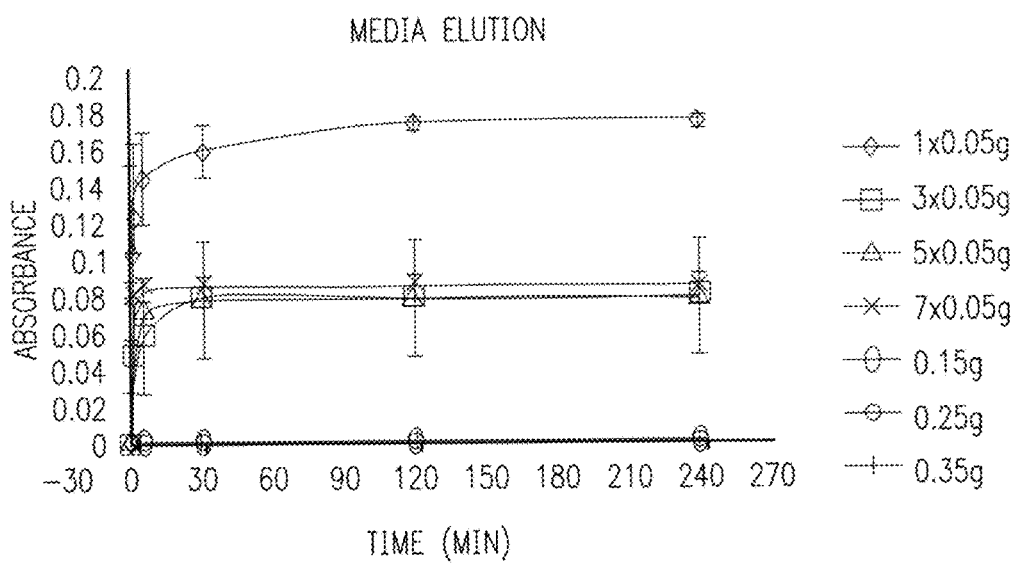

Referring to FIG. 8, Example 5 is an experiment to test the effect of a plurality of distinct laminated layers on therapeutic elution verses a comparable single layer. Selected as the test therapeutic was Doxorubicin HCl. The experiment has two parts utilizing two different solvents. The first part of the study is the elution of doxorubicin in water for which Doxorubicin is very soluble. The second part of the study is the elution of doxorubicin in media to mimic physiological conditions (DMEM media, 37 degrees Celsius, 5% carbon dioxide).

The following drug elution devices using regular parylene C that was not oxidatively functionalized where constructed:

| Type | Layers | Total Deposition |
|---|---|---|
| Control | 1 × 1.5 grams | 0.15 grams |
| (single layer) | 1 × 2.5 grams | 0.25 grams |
| | 1 × 3.5 grams | 0.35 grams |
| | 1 × 0.05 grams | 0.05 grams |
| Invention | 3 × 0.05 grams | 0.15 grams |
| (multilayer | 5 × 0.05 grams | 0.25 grams |
| laminate) | 7 × 0.05 grams | 0.35 grams |

Each of the devices was placed in 12 well plates in 1 milliliter of media or water as a solvent at room temperature (approximately 23 degrees Celsius). The devices were transferred to fresh wells containing 1 milliliter of solvent at the specified time points and the eluate was analyzed in a DU® Series 530 UV/vis (ultraviolet/visible) Spectrophotometer (Beckman Coulter, Fullerton, Calif.). For each time point, peak absorbance was measured at 490 nanometers at which Doxorubicin is readily detectable. The graphed result is the average of three datasets. All error bars are the standard deviations of the plotted data as calculated by the three replicates.

The data indicates that in media, a multilayer laminate construct of 3×0.05, 5×0.05 and 7×0.05 grams have approximately the same elution profile and that these devices release less drug that a single layer device of 0.05 gram laminate. Single layer laminate devices of 0.15, 0.25, and 0.35 grams do not release the drug in media. Using water for elution, in which the Doxorubicin-HCl has a much greater solubility, the elution profiles are much different. In water, a multilayer laminate construct of 1×0.05, 3×0.05, 5×0.05 and 7×0.05 grams have approximately the same elution profile. Single layer laminate devices of 0.15 and 0.25 grams have slower elution of the drug as expected from the thicker laminate coating. The single layer laminate device of 0.35 grams does not release the drug in water.

Example 6

Referring to FIG. 11, Example 6 is an experiment to test the elution of IgG-FITC in devices according to the present invention. IgG is a multipeptide chain protein of approximately 150 kD (kiloDaltons).

Protein addition to a base layer of parylene C was accomplished via desiccation of 100 µg IgG-FITC (KPL, Inc., Gaithersburg, Md.) under a laminar flow hood. Trilayer devices were constructed having no top barrier layer (uncovered,) a top barrier layer having a mass of 0.1 gram regular (not oxidized) parylene and a top barrier layer having a mass of 0.2 gram oxidized parylene.

Release studies were performed in conditions to mimic a physiological environment: DMEM Media (Hyclone, supra), 37 degrees Celsius, 5% carbon dioxide. The solvent was exchanged at the indicated time points and was monitored for released IgG-FITC using an fMax fluorimeter (Molecular Devices, supra, excitation—485 nm (nanometers), emission—538 nm).

Figure 11A:
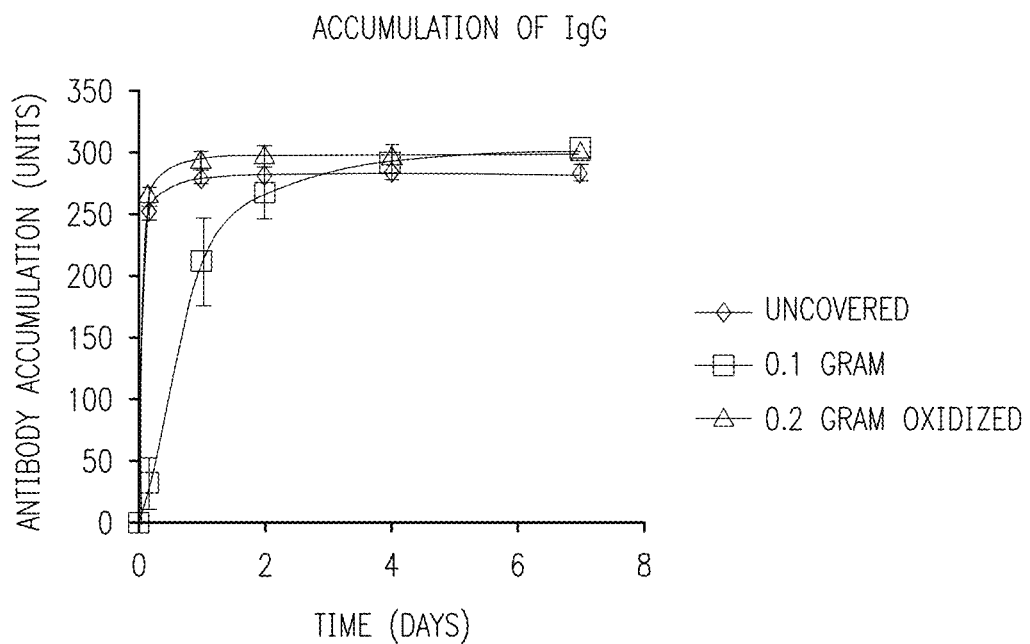
FIG. 11A is a graph showing IgG-FITC elution profiles for (i) a bilayer device having an oxidized parylene monolayer base; (ii) a trilayer device having the same base and an regular parylene monolayer top barrier layer and (iii) a tri-layer device having the same base and an oxidized parylene monolayer microfilm according to the present invention as a top barrier layer
Figure 11B:
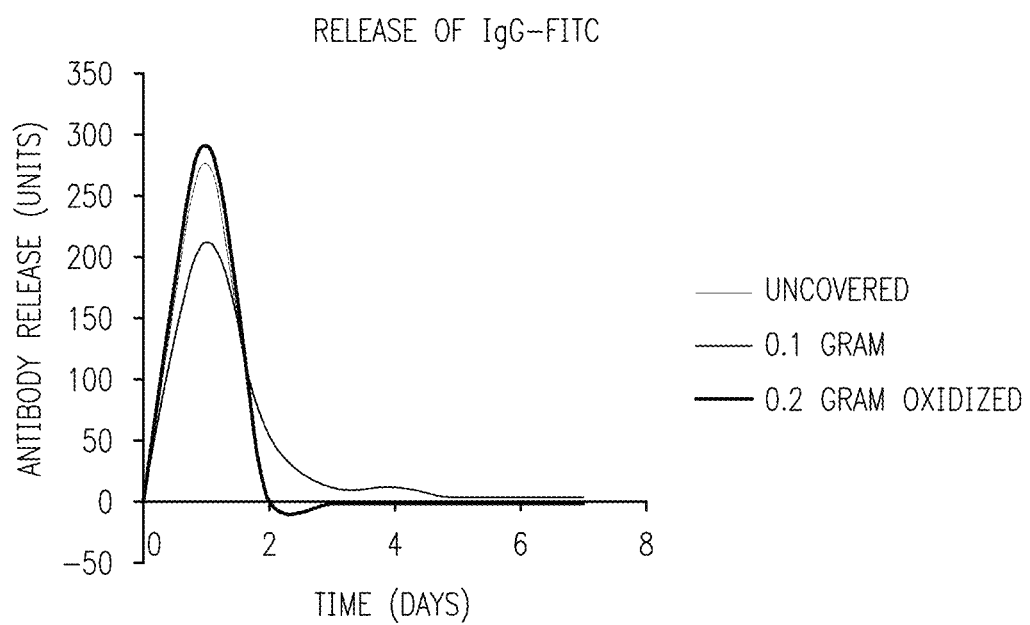
FIG. 11B is a graph showing the average release per day of IgG-FITC from the devices in FIG. 11A.

FIG. 11A is a graph of accumulated release and FIG. 11B is a graph of daily releases. All error bars are the standard deviations of the plotted data as calculated by three replicates of the experimental procedure. The data demonstrate the capacity of a film comprised of only parylene to capture and release a protein of approximately 150 kD (kiloDaltons) in size in a controlled manner through a porous parylene layer. The oxidization of the parylene film increases the elution of the captured protein. For example, in this case, even though double the amount of parylene (0.2 grams) was used to create the oxidized laminate layer than was used to create the unmodified laminate layer (0.1 grams), a greater elution rate was seen from the oxidized laminate device.

Example 7

Figure 12A:
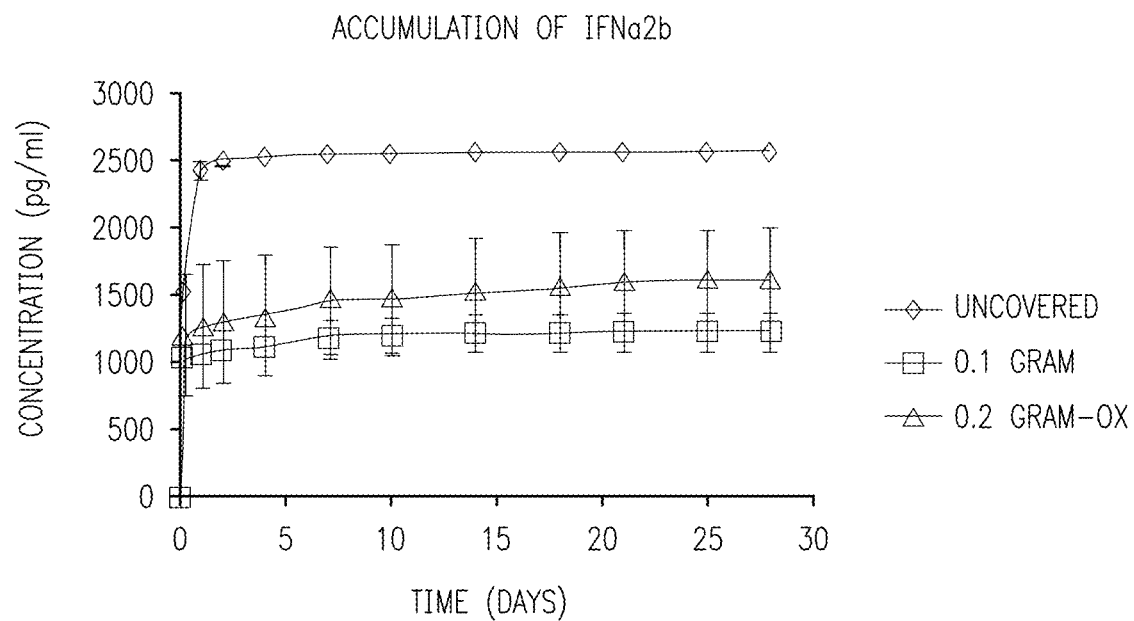
FIG. 12A is a graph showing interferonα2b elution profiles for (i) a bilayer device having an oxidized parylene monolayer base; (ii) a trilayer device having the same base and an regular parylene monolayer top barrier layer and (iii) a tri-layer device having the same base and an oxidized parylene monolayer microfilm according to the present invention as a top barrier layer
Figure 12B:
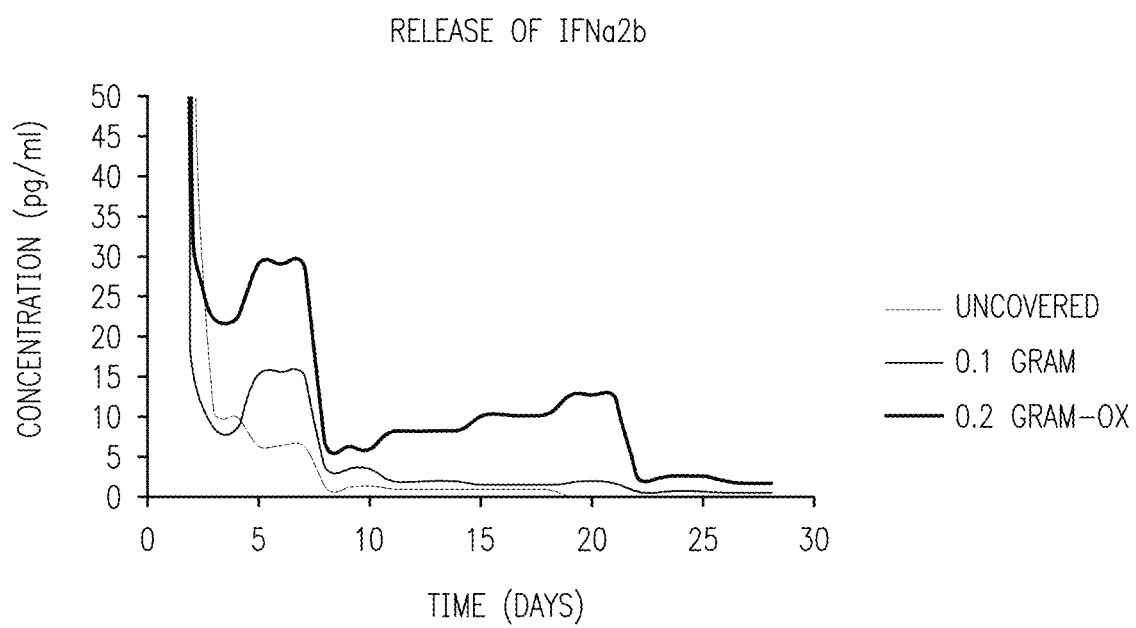
FIG. 12B is a graph showing the average release per day of interferonα2b from the devices highlighted in FIG. 12A.

Referring to FIG. 12, Example 7 is an experiment to test the elution of Interferonα2b in devices according to the present invention. Interferonα2b is a large protein.

Protein addition to the base layer of parylene C was accomplished via desiccation of 1 µg Interferon-α2b (IFN-α2b, Cell Sciences, Canton, Ma.) under a laminar flow hood. Trilayer devices were constructed having no top barrier layer (uncovered,) a top barrier layer having a mass of 0.1 gram regular (not oxidized) parylene; a top barrier layer having a mass of 0.2 gram oxidized parylene.

Release studies were performed in conditions to mimic a physiological environment: DMEM Media (Hyclone, supra), 37 degrees Celsius, 5% carbon dioxide. The solvent was exchanged at the indicated time points and was monitored for released IFN-α2b via ELISA (Bender Medsystems, Vienna, Austria) technology using a vMax absorbance plate reader as per manufactererer's guidelines (Molecular Devices, supra).

The data demonstrates the capacity of a film comprised of only parylene to capture and release an approximately 20 kilodalton protein in a controlled manner through a porous parylene layer and that the oxidization of the parylene film increases the duration of the elution of the captured protein. For example, in this case the initial burst release of IFN-α2b from devices containing an unmodified 0.1 gram or 0.2 gram oxidized laminate layer was comparable. However, release from the 0.2 gram oxidized device continued through 28 days while release from the 0.1 gram unmodified device tapered off at approximately 10 days.

Example 8

Figure 13A:
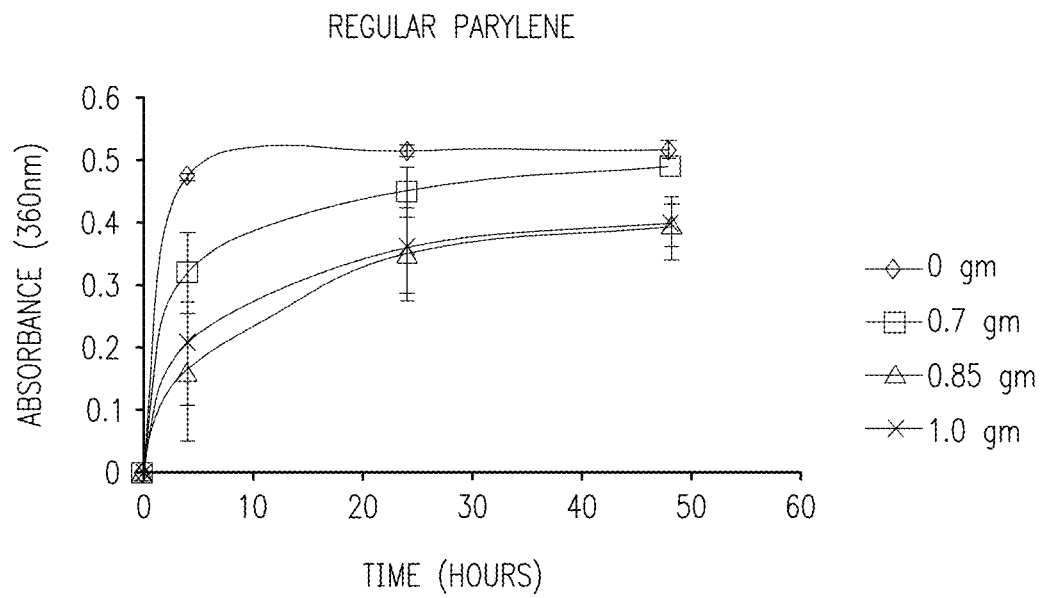
FIG. 13A is a graph showing mitomycin elution profiles for trilayer devices having an oxidized parylene monolayer base and three different thickness regular parylene barrier layer microfilms.
Figure 13B:
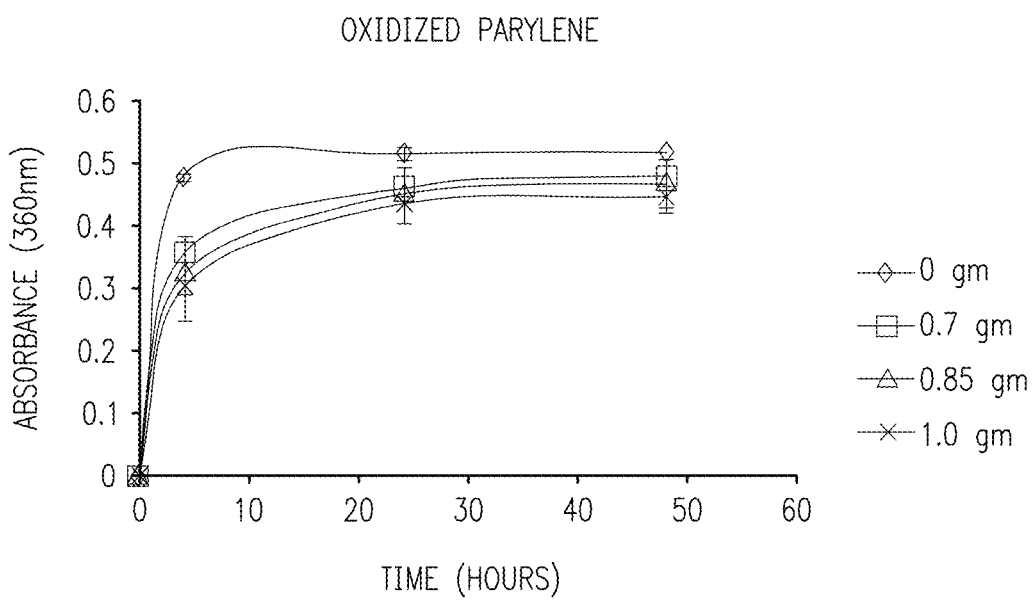
FIG. 13B is a graph showing mitomycin elution profiles for the same thickness microfilms with oxidized parylene according to the present invention and FIG. 14A is a graph showing paclitaxel elution profiles for trilayer devices having an oxidized parylene monolayer base and an oxidized parylene monolayer according to the present invention as a top barrier layer and FIG. 14B is a graph showing the average release per day of paclitaxel from the devices highlighted in FIG. 14A.

Referring to FIG. 13, Example 8 is an experiment to test the elution of Mitomycin in devices according to the present invention. Mitomycin is small, water soluble drug having a chemical composition of [(1aS,8S,8aR,8bS)-6-amino-8a-methoxy-5-methyl-4,7-dioxo-1,1a,2,4,7,8,8a,8b-octahydroazireno[2',3':3,4]pyrrolo[1,2-a]indol-8-yl]methyl carbamate. It is a DNA crosslinker with anti-cancer, anti-microbial, and anti-fungal activities.

Drug addition to the base layer of parylene C was accomplished via desiccation of 10 µl of a 0.5 mg/ml solution (5 µg total) of Mitomycin (Sigma-Aldrich, St. Louis, Mo.) under a laminar flow hood. A first series of trilayer devices were constructed having no top barrier layer (uncovered), a top barrier layer having a mass of 0.7, 0.85, or 1.0 gram regular (not oxidized) parylene. A second series of trilayer devices were constructed having no top barrier layer (uncovered), a top barrier layer having a mass of 0.7, 0.85, or 1.0 gram oxidized parylene.

Release studies were performed in phosphate buffered saline (PBS) at 37 degrees Celsius and 5% carbon dioxide. The solvent was exchanged at the indicated time points and was monitored for released Mitomycin in a DU® Series 530 UV/vis Spectrophotometer (Beckman Coulter, supra). For each time point, peak absorbance was measured at 360 nanometers at which Mitomycin is readily detectable.

The data demonstrate the capacity for the small, water soluble drug, mitomycin, to be packaged and released from the parylene device and expands upon the capabilities of the parylene microfilm device. The laminate layers required for harnessing and controlling the release of mitomycin are much thicker than that used for harnessing any of the therapeutics monitored previously. This shows the variety of laminate architecture that is possible for use in these parylene microfilm devices. Oxidation of the parylene laminate layers increases the release rate of the harnessed mitomycin, again demonstrating the advantage of creating a thicker, and thus more durable, porous parylene layer for controlled drug release.

Example 9

Figure 14A:
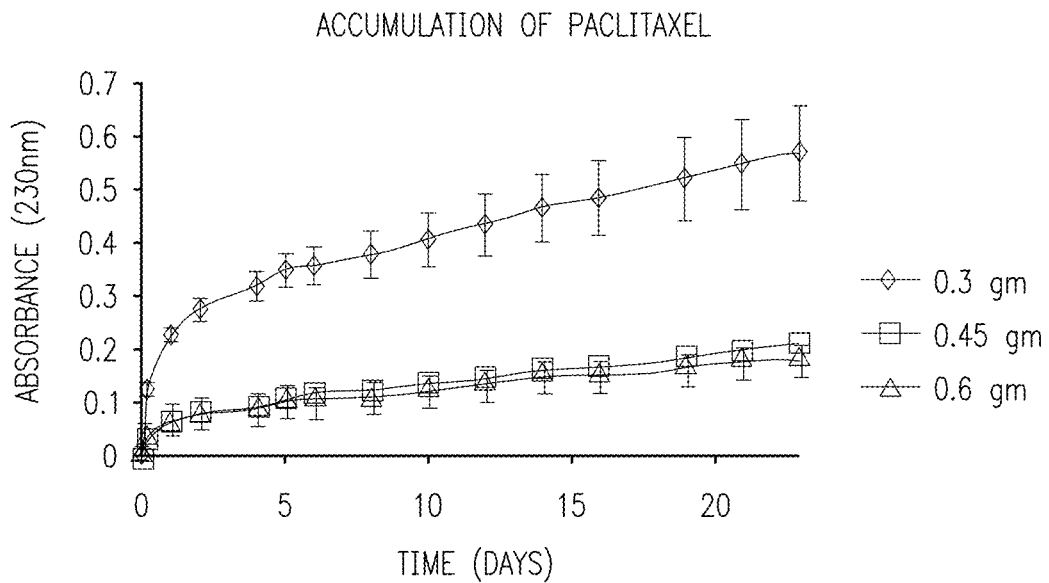
Figure 14B:
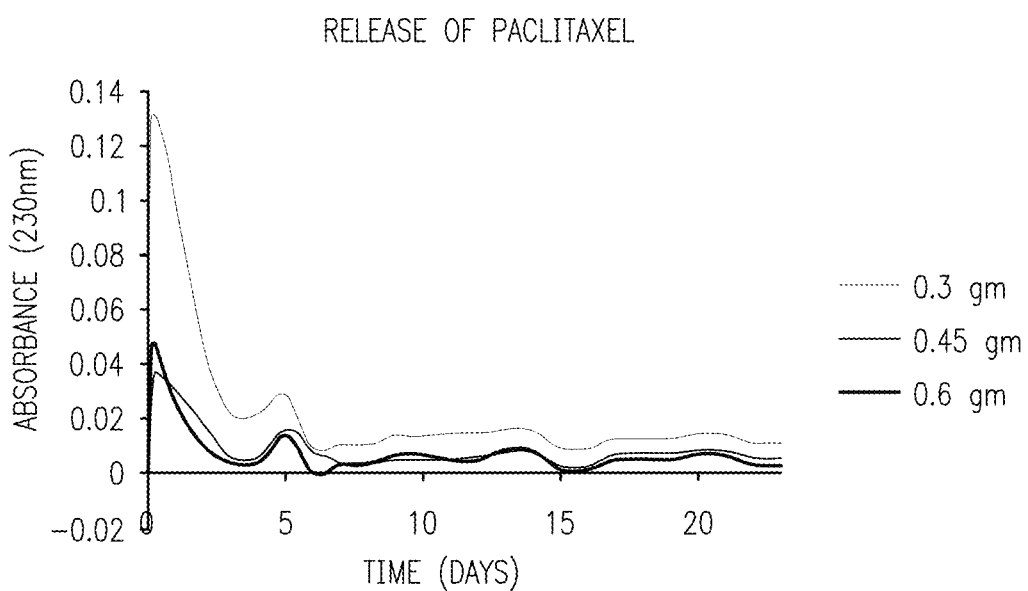

Referring to FIG. 14, Example 9 is an experiment to test the elution of paclitaxel (taxol). Paclitaxel is smaller hydrophobic molecule drug and has the chemical composition of (2α,4α,5β,7β,10β,13α)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate. It is a microtubule stabilizing therapeutic with anti-cancer properties.

Drug addition to the base layer of parylene C was accomplished via desiccation of 20 μl (microliters) of a 1.25 mg/ml (milligrams per milliliter) solution (25 μg total) of paclitaxel (Invitrogen, supra) under a laminar flow hood. A series of trilayer devices were constructed having a top barrier layer having a mass of 0.3, 0.45, or 0.6 gram oxidized parylene. Release studies were performed in phosphate buffered saline (PBS) at 37 degrees Celsius and 5% carbon dioxide.

Devices containing no top layer (uncovered) were not maintained as part of these experiments in that all of the drug is released from uncovered devices within the first 24 hours. It is theorized this rapid release may be attributable to the drug "falling off" the oxidized parylene surface since the dried drug does not really have anything holding it onto the surface of the microfilm in a liquid. With rapidly increasing concentration, the paclitaxel rapidly precipitates out of solution (visible by the accumulation of white precipitate) making quantification of the released drug impossible. Drug release from uncovered devices was determinable by the visualization of the devices and noticing the lack of drug on their surfaces.

As indicated, the release studies were performed in phosphate buffered saline (PBS) at 37 degrees Celsius and 5% carbon dioxide. The solvent was exchanged at the indicated time points and was monitored for released paclitaxel in a DU® Series 530 UV/vis Spectrophotometer (Beckman Coulter, supra). For each time point, peak absorbance was measured at 230 nanometers at which paclitaxel is readily detectable.

The data demonstrates the capacity for the small, hydrophobic drug, paclitaxel, to be packaged and released from the oxidized parylene device and expands upon the capabilities of the parylene microfilm device. The laminate layers required for harnessing and controlling the release of paclitaxel are all oxidized to decrease the likelihood of the drug sticking to a hydrophobic unmodified parylene surface.

Although the present invention has been described in considerable detail with reference to certain preferred versions thereof, other versions are possible with substituted, varied and/or modified materials and steps are employed. These other versions do not depart from the invention. Therefore, the spirit and scope of the appended claims should not be limited to the description of the preferred versions contained herein.

What is claimed:

1. A stand-alone controlled elution device comprised of:
   A. a reservoir that is comprised of at least one therapeutic and
   B. a microfilm that is porous that encapsulates the reservoir where the microfilm is selected from the group consisting of: (i)—microfilms that are comprised of para-xylylene polymer endowed with oxidatively functionalized para-xylene units and (ii) microfilms that are a multilayer laminate of a plurality of layers of para-xylylene polymer that is endowed with oxidatively functionalized para-xylene units, where there is a plurality of oxidatively functionalized para-xylene units and where the oxidatively functionalized para-xylene unit is a ring opened monomer derivatized with a functional group selected from the group consisting of —OH, —COO—, —C=O, or —CO—.

2. The stand-alone controlled elution device of claim 1 further comprised of one or more additional bilayers in an overlying arrangement comprised of:
   i. a reservoir that is comprised of at least one therapeutic disposed about an underlying microfilm and
   ii. a microfilm that is porous comprised of para-xylylene polymer endowed with oxidatively functionalized para-xylene units that is disposed about said underlying reservoir, where there is a plurality of oxidatively functionalized para-xylene units and where the oxidatively functionalized para-xylene unit is a ring opened monomer derivatized with a functional group selected from the group consisting of —OH, —COO—, —C=O, or —CO—.

3. A stand-alone capable controlled elution device comprised of:
   A. a microfilm base where the microfilm is selected from the group consisting of: (i) a microfilm that is comprised of para-xylylene polymer endowed with oxidatively functionalized para-xylene units and (ii) a microfilm that is a multilayer laminate of a plurality of layers of para-xylylene polymer that is endowed with oxidatively functionalized para-xylene units, where there is a plurality of oxidatively functionalized para-xylene units and where the oxidatively functionalized para-xylene unit is a ring opened monomer derivatized with a functional group selected from the group consisting of —OH, —COO—, —C=O, or —CO— and
   B. a reservoir of at least one therapeutic disposed about the microfilm base.

4. The stand-alone capable controlled elution device of claim 3 further comprised of one or more additional bilayers in an overlying arrangement comprised of:
   i. a microfilm that is porous that is disposed about an underlying reservoir and
   ii. a reservoir that is comprised of at least one therapeutic disposed about an underlying microfilm, where the microfilm is selected from the group consisting of: (i) a microfilm that is comprised of para-xylylene polymer endowed with oxidatively functionalized para-xylene units and (ii) a microfilm that is a multilayer laminate of a plurality of layers of para-xylylene polymer that is endowed with oxidatively functionalized para-xylene units, where there is a plurality of oxidatively functionalized para-xylene units and where the oxidatively functionalized para-xylene unit is a ring opened monomer derivatized with a functional group selected from the group consisting of —OH, —COO—, —C=O, or —CO—.

5. The stand-alone capable controlled elution device of claim 4 having a covering top microfilm.

6. A controlled elution system comprised of:
   A. a base;
   B. a reservoir that is comprised of at least one therapeutic disposed about the base and
   C. a microfilm comprised of para-xylylene polymer endowed with oxidatively functionalized para-xylene units disposed about the reservoir, where the microfilm is selected from the group consisting of: (i) microfilms that are comprised of para-xylylene polymer endowed with oxidatively functionalized para-xylene units and (ii) microfilms that are a multilayer laminate of a plurality of layers of para-xylylene polymer that is endowed with oxidatively functionalized para-xylene units,
      where there is a plurality of oxidatively functionalized para-xylene units and where the oxidatively functionalized para-xylene unit is a ring opened monomer derivatized with a functional group selected from the group consisting of —OH, —COO—, —C=O, or —CO—.

7. The controlled elution system of claim 6 where the base is a microfilm having a first side and a second side, where the reservoir of claim element 4B that is comprised of at least one therapeutic disposed about the base is a first reservoir and the at least one therapeutic is disposed about said first side of the base and where the microfilm of claim element 4C is a first microfilm disposed about the first reservoir and additionally comprising:
- A. a second reservoir comprised of at least one therapeutic disposed about said second side of the microfilm base and
- B. a second microfilm that is porous that disposed about said second reservoir that is selected from the group consisting of: (i) microfilms that are comprised of para-xylylene polymer endowed with oxidatively functionalized para-xylene units and (ii) microfilms that are a multilayer laminate of a pluarity of layers of para-xylylene polymer that is endowed with oxidatively functionalized para-xylene units, where there is a pluarity of oxidatively functionalized para-xylene units and where the oxidatively functionalized para-xylene unit is a ring opened monomer derivatized with a functional group selected from the group consisting of —OH, —COO—, —C=O, or —CO—.

* * * * *